(12) United States Patent
Dutta et al.

(10) Patent No.: US 9,164,080 B2
(45) Date of Patent: Oct. 20, 2015

(54) SYSTEM AND METHOD FOR SENSING NO

(75) Inventors: Prabir K. Dutta, Worthington, OH (US); Suvra P. Mondal, Purba Medinopore (IN)

(73) Assignee: Ohio State Innovation Foundation, Columbus, OH (US)

(*) Notice: Subject to any disclaimer, the term of this patent is extended or adjusted under 35 U.S.C. 154(b) by 515 days.

(21) Appl. No.: 13/493,846

(22) Filed: Jun. 11, 2012

(65) Prior Publication Data

US 2013/0327122 A1 Dec. 12, 2013

(51) Int. Cl.
G01N 33/497 (2006.01)
G01N 33/00 (2006.01)

(52) U.S. Cl.
CPC .......... *G01N 33/497* (2013.01); *G01N 33/0037* (2013.01); *G01N 2033/4975* (2013.01)

(58) Field of Classification Search
CPC ................. G01N 2033/4975; G01N 33/0037; G01N 33/497
See application file for complete search history.

(56) References Cited

U.S. PATENT DOCUMENTS

| 3,843,400 A | 10/1974 | Radford et al. |
| 4,025,412 A | 5/1977 | LaConti |
| 4,171,253 A | 10/1979 | Nolan et al. |
| 4,227,984 A | 10/1980 | Dempsey et al. |
| 4,265,714 A | 5/1981 | Nolan et al. |
| 4,358,950 A | 11/1982 | Chang Shih-Chia et al. |
| 4,505,807 A | 3/1985 | Yamada |
| 4,703,646 A | 11/1987 | Muller et al. |
| 4,770,760 A | 9/1988 | Noda et al. |
| 4,886,584 A | 12/1989 | Cheng |
| 4,927,517 A | 5/1990 | Mizutani et al. |
| 5,128,020 A | 7/1992 | Yamauchi et al. |
| 5,389,218 A | 2/1995 | Bonne et al. |
| 5,460,711 A | 10/1995 | Riegel et al. |
| 5,476,001 A | 12/1995 | Hoetzel et al. |
| 5,493,896 A | 2/1996 | Riegel |
| 5,505,837 A | 4/1996 | Friese et al. |
| 5,595,647 A | 1/1997 | Hoetzel et al. |
| 5,624,640 A | 4/1997 | Potthast et al. |
| 5,672,811 A | 9/1997 | Kato et al. |
| 5,763,763 A | 6/1998 | Kato et al. |

(Continued)

FOREIGN PATENT DOCUMENTS

WO  WO 2008103311 A9 * 6/2009

OTHER PUBLICATIONS

Yang, Jiun-Chan, and Prabir K. Dutta. "Solution-based synthesis of efficient $WO_3$ sensing electrodes for high temperature potentiometric $NO_x$ sensors." Sensors and Actuators B: Chemical 136.2 (2009): 523-529.*

(Continued)

*Primary Examiner* — Lisa Caputo
*Assistant Examiner* — Punam Roy
(74) *Attorney, Agent, or Firm* — Meunier Carlin & Curfman LLC

(57) ABSTRACT

An NO sensing system includes an inlet for receiving an original sample, a humidifier, fluidly communicating with the inlet, and a first sensor. The original sample is fluidly transmitted through the humidifier and exits the humidifier as a humidified sample having a humidity above a predetermined level. The first sensor generates a potential difference in response to presence of NO in the humidified sample. The potential difference is indicative of a level of NO within the original sample.

20 Claims, 16 Drawing Sheets

(56) References Cited

U.S. PATENT DOCUMENTS

| | | |
|---|---|---|
| 5,767,386 A | 6/1998 | Lemire et al. |
| 5,811,661 A | 9/1998 | Scheid et al. |
| 5,827,415 A | 10/1998 | Gur et al. |
| 5,861,092 A | 1/1999 | Kiyota et al. |
| 5,866,799 A | 2/1999 | Kato et al. |
| 5,877,406 A | 3/1999 | Kato et al. |
| 5,897,759 A | 4/1999 | Kurosawa et al. |
| 5,902,469 A | 5/1999 | Kato et al. |
| 5,928,494 A | 7/1999 | Kato et al. |
| 5,939,615 A | 8/1999 | Kato et al. |
| 5,942,190 A | 8/1999 | Kato et al. |
| 5,948,963 A | 9/1999 | Kato et al. |
| 5,948,964 A | 9/1999 | Kato |
| 5,953,907 A | 9/1999 | Kato et al. |
| 5,976,335 A | 11/1999 | Kato et al. |
| 5,997,707 A | 12/1999 | Kato et al. |
| 6,006,586 A | 12/1999 | Yoshida et al. |
| 6,010,459 A | 1/2000 | Silkoff et al. |
| 6,010,615 A | 1/2000 | Kato et al. |
| 6,012,327 A | 1/2000 | Seth et al. |
| 6,019,881 A | 2/2000 | Kurosawa et al. |
| 6,036,841 A | 3/2000 | Kato et al. |
| 6,038,913 A | 3/2000 | Gustafsson et al. |
| 6,071,393 A | 6/2000 | Oshima et al. |
| 6,076,393 A | 6/2000 | Kato et al. |
| 6,082,176 A | 7/2000 | Kondo et al. |
| 6,093,294 A | 7/2000 | Kato et al. |
| 6,099,480 A | 8/2000 | Gustafsson |
| 6,101,865 A | 8/2000 | Meixner et al. |
| 6,110,348 A | 8/2000 | Sugiyama et al. |
| 6,126,902 A | 10/2000 | Kunimoto et al. |
| 6,156,175 A | 12/2000 | Kato et al. |
| 6,179,992 B1 | 1/2001 | Nafe et al. |
| 6,190,039 B1 | 2/2001 | Yaguchi |
| 6,196,053 B1 | 3/2001 | Kato et al. |
| 6,214,207 B1 | 4/2001 | Miyata et al. |
| 6,224,727 B1 | 5/2001 | Miyata et al. |
| 6,228,252 B1 | 5/2001 | Miyata et al. |
| 6,235,243 B1 | 5/2001 | Fleischer et al. |
| 6,258,232 B1 | 7/2001 | Hasegawa et al. |
| 6,280,588 B1 | 8/2001 | Kato et al. |
| 6,284,112 B1 | 9/2001 | Kato et al. |
| 6,287,439 B1 | 9/2001 | Kato et al. |
| 6,289,719 B1 | 9/2001 | Bloemer et al. |
| 6,290,840 B1 | 9/2001 | Kato et al. |
| 6,295,862 B1 | 10/2001 | Kurokawa et al. |
| 6,296,748 B1 | 10/2001 | Ohtsuki et al. |
| 6,306,271 B1 | 10/2001 | Kato et al. |
| 6,306,677 B1 | 10/2001 | Vargo et al. |
| 6,319,377 B1 | 11/2001 | Hasei et al. |
| 6,327,891 B1 | 12/2001 | Noda et al. |
| 6,332,965 B1 | 12/2001 | Sugiyama et al. |
| 6,336,354 B1 | 1/2002 | Suzuki et al. |
| 6,341,599 B1 | 1/2002 | Hada et al. |
| 6,344,119 B2 | 2/2002 | Kato et al. |
| 6,344,134 B1 | 2/2002 | Yamada et al. |
| 6,346,178 B1 | 2/2002 | Lankheet |
| 6,348,140 B1 | 2/2002 | Matsubara et al. |
| 6,348,141 B1 | 2/2002 | Kato et al. |
| 6,352,632 B1 | 3/2002 | Inagaki et al. |
| 6,355,152 B1 | 3/2002 | Kato et al. |
| 6,365,880 B1 | 4/2002 | Kikuchi et al. |
| 6,375,828 B2 | 4/2002 | Ando et al. |
| 6,383,354 B1 | 5/2002 | Kurokawa et al. |
| 6,395,161 B1 | 5/2002 | Schneider et al. |
| 6,397,659 B1 | 6/2002 | Mizoguchi et al. |
| 6,419,818 B2 | 7/2002 | Kato et al. |
| 6,429,410 B2 | 8/2002 | Koch |
| 6,435,005 B1 | 8/2002 | Kikuchi et al. |
| 6,442,998 B2 | 9/2002 | Kurokawa et al. |
| 6,453,724 B1 | 9/2002 | Kawase et al. |
| 6,468,407 B2 | 10/2002 | Clyde et al. |
| 6,478,941 B2 | 11/2002 | E et al. |
| 6,486,449 B2 | 11/2002 | Kikuchi et al. |
| 6,495,027 B1 | 12/2002 | Stahl et al. |
| 6,497,808 B1 | 12/2002 | Yamauchi et al. |
| 6,514,397 B2 | 2/2003 | LaBarge et al. |
| 6,517,702 B2 | 2/2003 | Stahl |
| 6,527,929 B2 | 3/2003 | Kato et al. |
| 6,533,911 B1 | 3/2003 | Fujita et al. |
| 6,533,921 B2 | 3/2003 | Miyata et al. |
| 6,540,892 B1 | 4/2003 | Strohmaier |
| 6,544,394 B1 | 4/2003 | Strohmaier et al. |
| 6,547,955 B1 | 4/2003 | Hada et al. |
| 6,548,023 B1 | 4/2003 | Matsuo et al. |
| 6,551,497 B1 | 4/2003 | Gao et al. |
| 6,554,983 B2 | 4/2003 | Imamura et al. |
| 6,562,215 B1 | 5/2003 | Nelson et al. |
| 6,565,723 B1 | 5/2003 | Danley et al. |
| 6,579,435 B2 | 6/2003 | Wang et al. |
| 6,598,596 B2 | 7/2003 | Wachsman et al. |
| 6,616,820 B2 | 9/2003 | Wang et al. |
| 6,618,927 B2 | 9/2003 | Tajima et al. |
| 6,623,617 B2 | 9/2003 | Ando |
| 6,623,618 B1 | 9/2003 | Kato et al. |
| 6,632,338 B2 | 10/2003 | Fujii et al. |
| 6,635,162 B2 | 10/2003 | Sugaya et al. |
| 6,638,405 B2 | 10/2003 | Jain et al. |
| 6,645,361 B1 | 11/2003 | Bloemer et al. |
| 6,656,337 B2 | 12/2003 | Kurokawa et al. |
| 6,663,756 B2 | 12/2003 | Lee et al. |
| 6,673,223 B2 | 1/2004 | Kunimoto et al. |
| 6,682,640 B2 | 1/2004 | Jain et al. |
| 6,689,266 B2 | 2/2004 | Kato et al. |
| 6,695,964 B1 | 2/2004 | Ando et al. |
| 6,709,558 B2 | 3/2004 | LaBarge |
| 6,723,056 B1 | 4/2004 | Alving et al. |
| 6,723,217 B1 | 4/2004 | Duce et al. |
| 6,733,463 B2 | 5/2004 | Moilanen et al. |
| 6,740,217 B2 | 5/2004 | Mizutani et al. |
| 6,764,591 B1 | 7/2004 | Dutta et al. |
| 6,767,442 B1 | 7/2004 | Scheer et al. |
| 6,773,565 B2 | 8/2004 | Kunimoto et al. |
| 6,776,890 B1 | 8/2004 | Mueller et al. |
| 6,787,014 B2 | 9/2004 | Hasei et al. |
| 6,793,788 B2 | 9/2004 | Wang et al. |
| 6,797,138 B1 | 9/2004 | Detwiler et al. |
| 6,824,661 B2 | 11/2004 | Lawless |
| 6,843,900 B2 | 1/2005 | Dutta et al. |
| 6,849,174 B2 | 2/2005 | Hada et al. |
| 6,849,291 B2 | 2/2005 | E et al. |
| 6,911,140 B2 | 6/2005 | Springhorn et al. |
| 6,916,415 B2 | 7/2005 | Walde |
| 6,923,902 B2 | 8/2005 | Ando et al. |
| 6,936,149 B2 | 8/2005 | Wahl et al. |
| 6,960,476 B2 | 11/2005 | Morris |
| 6,966,978 B2 | 11/2005 | Ketterle et al. |
| 6,984,298 B2 | 1/2006 | Polikarpus et al. |
| 7,013,701 B2 | 3/2006 | Kawashima |
| 7,036,982 B2 | 5/2006 | Smith et al. |
| 7,037,415 B2 | 5/2006 | Cramer et al. |
| 7,045,047 B2 | 5/2006 | Nakae et al. |
| 7,048,844 B2 | 5/2006 | Chen et al. |
| 7,052,595 B2 | 5/2006 | Schulte et al. |
| 7,066,009 B2 | 6/2006 | Yamada |
| 7,073,320 B2 | 7/2006 | Moritsugu et al. |
| 7,097,875 B2 | 8/2006 | Clyde et al. |
| 7,128,818 B2 | 10/2006 | Khesin et al. |
| 7,138,604 B2 | 11/2006 | Polikarpus et al. |
| 7,142,976 B2 | 11/2006 | Inoue et al. |
| 7,153,401 B2 | 12/2006 | Martin et al. |
| 7,153,412 B2 | 12/2006 | Inaba et al. |
| 7,156,967 B2 | 1/2007 | Hotta et al. |
| 7,160,435 B2 | 1/2007 | Kato et al. |
| 7,170,731 B2 | 1/2007 | Wagner |
| 7,180,596 B2 | 2/2007 | Haraguchi et al. |
| 7,214,333 B2 | 5/2007 | Mukundan et al. |
| 7,217,355 B2 | 5/2007 | Nair et al. |
| 7,241,477 B2 | 7/2007 | Chang et al. |
| 7,244,316 B2 | 7/2007 | Jain et al. |
| 7,252,748 B2 | 8/2007 | Inoue |
| 7,264,700 B1 | 9/2007 | Garzon et al. |
| 2002/0046947 A1 | 4/2002 | Lawless |
| 2002/0100697 A1 | 8/2002 | Quinn et al. |

(56) References Cited

U.S. PATENT DOCUMENTS

| | | |
|---|---|---|
| 2003/0052004 A1 | 3/2003 | Isitani et al. |
| 2003/0121780 A1 | 7/2003 | Dutta et al. |
| 2006/0027465 A1 | 2/2006 | Nair et al. |
| 2006/0194330 A1 | 8/2006 | Nair et al. |
| 2007/0012566 A1 | 1/2007 | Nair et al. |
| 2007/0045114 A1 | 3/2007 | Wang et al. |
| 2007/0051641 A1 | 3/2007 | Kroot et al. |
| 2007/0289870 A1 | 12/2007 | Nair et al. |
| 2008/0017510 A1 | 1/2008 | Nair et al. |
| 2009/0260418 A1 | 10/2009 | Flaherty et al. |
| 2010/0137733 A1 | 6/2010 | Wang et al. |
| 2013/0219988 A1* | 8/2013 | Dutta et al. .................... 73/23.3 |

OTHER PUBLICATIONS

Fulmer, Adam, et al. "Novel strategies for development of gas sensors for combustion and medical applications." Proc. of SPIE vol. vol. 9083. Jun. 5, 2014.*

Hemmingsson, Tryggve, Dag Linnarsson, and Rudolf Gambert. "Novel hand-held device for exhaled nitric oxide-analysis in research and clinical applications." Journal of clinical monitoring and computing 18.5-6 (2004): 379-387.*

Chang, C. W., et al. "Design, fabrication, and testing of MEMS-based miniaturized potentiometric nitric oxide sensors." Sensors and Actuators B: Chemical 204 (2014): 183-189.*

Sun, Chenhu, G. Maduraiveeran, and Prabir Dutta. "Nitric oxide sensors using combination of p- and n-type semiconducting oxides and its application for detecting NO in human breath." Sensors and Actuators B: Chemical 186 (2013): 117-125.*

Vilar, M. Rei, et al. "Development of nitric oxide sensor for asthma attack prevention." Materials Science and Engineering: C 26.2 (2006): 253-259.*

Hunter, G. W., et al. "Smart sensor systems for human health breath monitoring applications." Journal of breath research 5.3 (Sep. 6, 2011): 037111.*

Yang, Jiun-Chan, and Prabir K. Dutta. "Promoting selectivity and sensitivity for a high temperature YSZ-based electrochemical total NO< sub> x</sub> sensor by using a Pt-loaded zeolite Y filter." Sensors and Actuators B: Chemical 125.1 (2007): 30-39.*

Di Bartolomeo et al., Solid State Ionics 171 (2004) 173-181.

Yang et al, Sensors and Actuators B 123 (2007) 929-936.

Young, Lee "International Search Report", PCT Application No. PCT/US08/02079 (Jun. 13, 2008) 1-2.

Young, Lee "Written Opinion of the International Searching Authority", PCT/US08/02079 (Jun. 13, 2008), 1-6.

Acke, Filip et al., "Comparison between ammonia and propene as the reducing agent in the selective catalytic reduction of NO under lean conditions over Pt black" Applied Catalysis B: Environmental, 20, (1999), 133-144.

Baier, G. et al., "Non-Nernstian Zirconia Sensors for Combustion Control", Appl. Phys A, 57 (1993), 51-56.

Benard, S. et al., "Supported platinum catalysts for nitrogen oxide sensors", Applied Catalysis B: Environmental, 55, (2005), 11-21.

Busca, Guido et al., "Chemical and mechanistic aspects of the selective catalytic reduction of NOx by ammonia over oxide catalysts: A review", Applied Catalysis B: Environmental, 18, (1998), 1-36.

Chambers, Dean C., et al., "The inhibition of propane oxidation by nitric oxide on a Pt/SiO2 catalyst", Applied Catalysis B: Environmental, 41, (2003), 61-70.

De Graaf, J. et al., "Preparation of Highly Dispersed Pt Particles in Zeolite Y with a Narrow Particle Size Distribution: Characterization by Hydrogen Chemisorption, TEM, EXAFS Spectroscopy, and Particle Modeling", Journal of Catalysis, 203, (2001), 307-321.

Despres, Joel et al., "Catalytic oxidation of nitrogen monoxide over Pt/SiO2", Applied Catalysis B: Environmental 50, (2004), 73-82.

Dutta, Atanu et al, "Study of YSZ-Based Electrochemical Sensors with WO3 Electrodes in NO2 and CO Environments", Journal of the Electrochemical Society, 150 (2), (2003), H33-H37.

Fleischer, Maximilian et al., "Selective gas detection with high-temperature operated metal oxides using catalytic filters", Sensors and Actuators B, 69, (2000), 205-210.

Fruhberger, B. et al., "Detection and quantification of nitric oxide in human breath using a semiconducting oxide based chemiresistive microsensor", Sensors and Actuators B, 76 (2001), 226-234.

Gopel, Wolfgang et al., "Trends in the development of solid state amperometric and potentiometric high temperature sensors", Solid State Ionics, 136-137 (2000), 519-531.

Gurlo, Alexander et al., "Polycrystalline Well-Shaped Blocks of Indium Oxide Obtained by the Sol-Gel Method and Their Gas-Sensing Properties", Chem. Mater, 2003, 15, (2003), 4377-4383.

Hadjiivanov, Konstantin "Identification of Neutral and Charged NxOy Surface Species by IR Spectroscopy", Catal. Rev.-Sci. Eng., 42 (1&2), (2000), 71-144.

Hadjiivanov, Konstantin et al., "Detection of reduced Wn+ sites on WO3—ZrO2 and Pt/WO3—ZrO2 catalysts by infrared spectroscopy of adsorbed NO", Catalysis Letters vol. 82, No. 1-2 (Sep. 2002), 73-77.

Hubalek, J. et al., "Pt-loaded Al2O3 catalytic filters for screen-printed WO3 sensors highly selective to benzene", Sensors and Actuators B, 101 (2004), 277-283.

Huuhtanen, Mika et al., "Pt-loaded zeolites for reducing exhaust gas emissions at low temperatures and in lean conditions", Catalysis Today, 100 (2005), 321-325.

Kitsukawa, S. et al., "The interference elimination for gas sensor by catalysts filters", Sensors and Actuators B, 65 (2000), 120-121.

Lu, G. et al., "Stabilized zirconia-based sensors using WO3 electrode for detection of NO or NO2," Sensors and Actuators B, 65 (2000), 125-127.

Martin, L. P., et at., "Effect of Cr2O3 electrode morphology on the nitric oxide response of a stabilized zirconia sensor", Sensors and Actuators B, 96 (2003), 53-60.

McIntosh, Steven et al., "Direct Hydrocabon Solid Oxide Fuel Cells", Chem. Rev. 104 (2004),4845-4865.

Menil, Francis et al., "Critical review of nitrogen monoxide sensors for exhaust gases of lean bum engines", Sensors and Actuators B, 67 (2000), 1-23.

Miura, Norio et al., "Progress in mixed-potential type devices based on solid electrolyte for sensing redox gases", Solid State Ionics, 136-137, (2000), 533-342.

Radhakrishnan, R. at al., "Design, fabrication and characterization of a miniaturized series-connected potentiometric oxygen sensor", Sensors and Actuators B, 105, (2005), 312-321.

Raj, Edwin S., et al., "High Conductivity La2—XSrxCU1—y(Mg,Al)yO4 Solid State Metal Oxide Gas Sensors with the K2NiF4 Structure", Chem. Mater., 2006, 18, (2006), 3351-3355.

Reinhardt, Gotz et al., "Sensing small molecules with amperometric sensors", Solid State Ionics 150, (2002), 79-92.

Seinfeld, J. H., et at, "Atmospheric Composition, Global Cycles, and Lifetimes", Atmospheric Chemistry and Physics: From Air Pollution to Climate Change, Wiley, New York, (1998), 70-74.

Szabo, Nicholas et al, "Strategies for total NOx measurement with minimal CO interference utilizing a microporous zeolitic catalytic filter", Sensors and Actuators B, 88 (2003), 168-177.

Szabo, Nicholas F., et al., "Correlation of sensing behavior of mixed potential sensors with chemical and electrochemical properties of electrodes", Solid State Ionics, 171 (2004), 183-190.

Taylor, "Nitric Oxide Catalysis in Automotive Exhaust Systems", Catalysis Reviews: Science and Engineering, 35 (4), (1993),457-481.

Yoo, Jiho et al., "Temperature-Programmed Reaction and Desorption of the Sensor Elements of a WO3/YSZ/Pt Potentiometric Sensor", Journal of the Electrochemical Society, 153 (6), (2006), H115-H121.

Olsen, Office Action for U.S. Appl. No. 11/137,693 sent Jul. 21, 2006, 1-12.

Olsen, Office Action for U.S. Appl. No. 11/182,278 sent Apr. 16, 2008, 1-12.

Olsen, International Search Report for PCT/US05/18545 sent Aug. 4, 2006,1-6.

Olsen Written Opinion for PCT/US05/18545 sent Aug. 4, 2006, 1-6.

Olsen, International Search Report for PCT/US06/27334 sent Apr. 25, 2008 1-3.

Olsen, Written Opinion for PCT/US06/27334 sent Apr. 25, 2008, 1-5.

(56) References Cited

OTHER PUBLICATIONS

Mondal, et al. "Development of high sensitivity potentiometric NOx sensor and its application to breath analysis", Sensors and Actuators B: Chemical published Jun. 12, 2011, pp. 1-7.
U.S. Election/Restriction Office Action for related U.S. Appl. No. 12/032,114, dated Feb. 16, 2011.
Response to Restriction Requirement for related U.S. Appl. No. 12/032,114, filed Mar. 1, 2011.
U.S. Non-Final Office Action for related U.S. Appl. No. 12/032,114, dated May 18, 2011.
Response to Non-Final Office Action for related U.S. Appl. No. 12/032,114, filed Nov. 15, 2011.
U.S. Final Office Action for related U.S. Appl. No. 12/032,114, dated Dec. 20, 2011.
Notice of Abandonment for related U.S. Appl. No. 12/032,114, dated Jul. 2, 2012.

* cited by examiner

US 9,164,080 B2

SYSTEM AND METHOD FOR SENSING NO

BACKGROUND

The present invention relates to detection of nitric oxide (NO). It finds particular application in conjunction with detection of NO in a vapor stream and will be described with particular reference thereto. It will be appreciated, however, that the invention is also amenable to other applications.

At times it is desirable to detect nitric oxide (NO). Different sensing strategies for detecting NO include optical spectroscopy, mass spectrometry, chromatography, chemiluminescence, and electrochemistry. Each of the sensing strategies has its advantages and disadvantages. The extent to which NO sensing devices may be miniaturized varies (e.g., solid-state electrochemical sensors).

It is desirable to detect NO in a parts per billion (ppb) range (e.g., in the 1 ppb-100 ppb range). It is also desirable to selectively detect NO against, for example, $CO_2$ and CO hydrocarbons in a vapor stream.

The present invention provides a new and improved apparatus and method which addresses the above-referenced problems.

SUMMARY

In one embodiment, an NO sensing system includes an inlet for receiving an original sample, a humidifier, fluidly communicating with the inlet, and a first sensor. The original sample is fluidly transmitted through the humidifier and exits the humidifier as a humidified sample having a humidity above a predetermined level. The first sensor generates a potential difference in response to presence of NO in the humidified sample. The potential difference is indicative of a level of NO within the original sample.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to exemplify the embodiments of this invention.

DETAILED DESCRIPTION OF ILLUSTRATED EMBODIMENT

Figure 1:
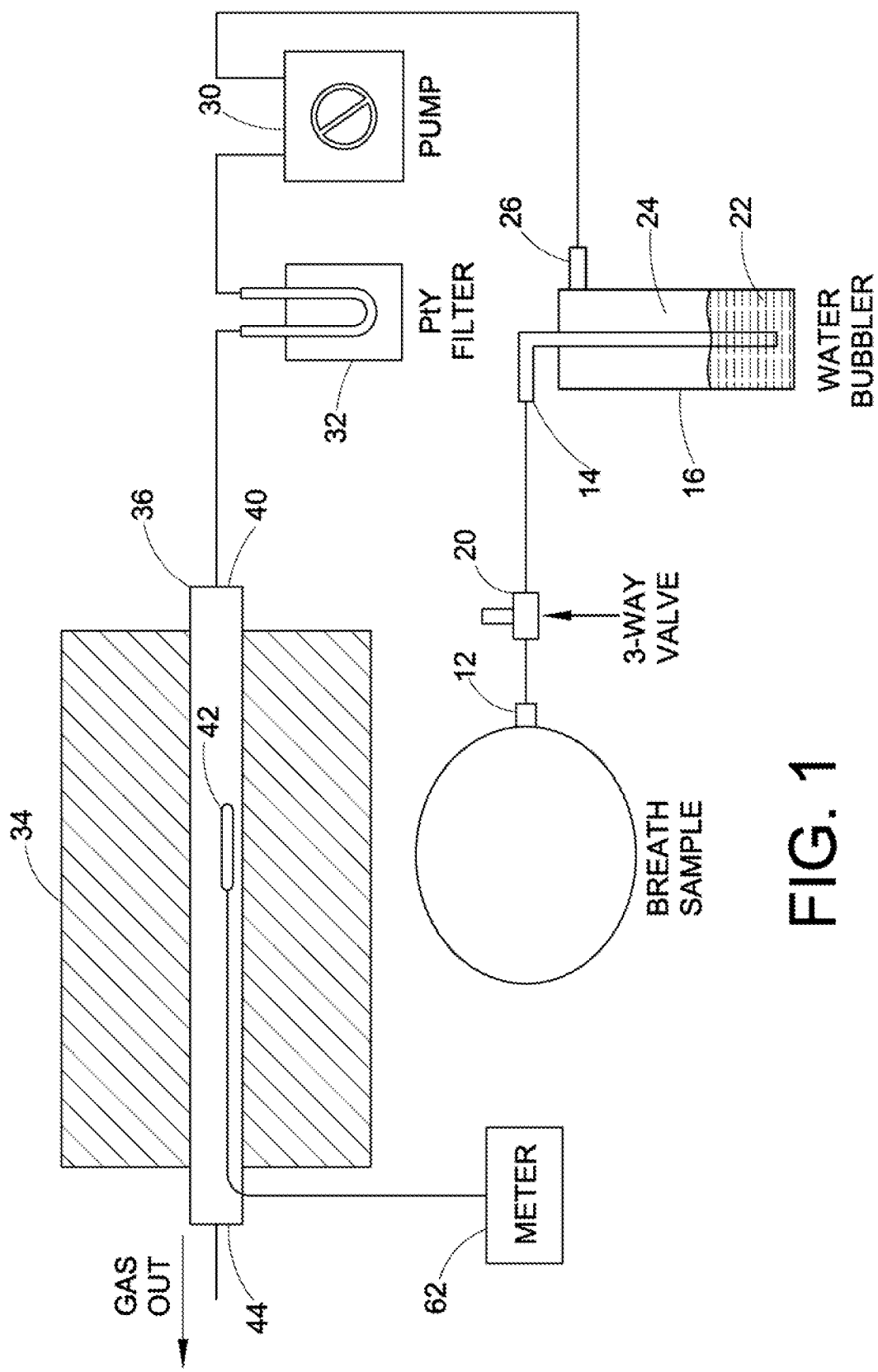
FIG. 1 illustrates a simplified component diagram of an exemplary NO sensing system in accordance with one embodiment of the present invention.

With reference to FIG. 1, a simplified component diagram of an exemplary NO sensing system 10 is illustrated in accordance with one embodiment of the present invention. The system 10 includes a system inlet 12 for receiving an original sample from, for example, a subject. In one embodiment, the original sample is a breath sample from the subject.

The system inlet 12 selectively fluidly communicates with an inlet 14 of a humidifier 16 via a 3-way valve 20. The 3-way valve 20 is selectively set to one (1) of two (2) different positions. In a first of the positions, the 3-way valve 20 is set so that the humidifier 16 fluidly communicates with the system inlet 12. In a second of the positions, the 3-way valve 20 is set so that the humidifier 16 fluidly communicates with atmosphere. The 3-way valve 20 is set to the second position for fluidly transmitting air as a reference sample to the humidifier 16. The reference sample provides a means for the system 10 to obtain a background signal. The 3-way valve 20 is set to the first position for fluidly transmitting the original sample (e.g., a breath sample) from the subject to the humidifier 16.

A liquid fluid 22 is included in the humidifier 16. The humidifier inlet 14 fluidly communicates the original sample directly into the fluid 22 inside the humidifier 16. Pressure created by the original sample causes the original sample to pass through the fluid 22. The pressure is created, for example, by an exhaling action of the subject. In other words, the subject is blowing the original sample into the fluid 22. The original sample exits the fluid 22 into a chamber 24 inside the humidifier 16. Since the original sample is a gas, the original sample bubbles through the fluid 22 inside the humidifier 16. It is contemplated that the original sample is exhaled breath of a subject. However, other embodiments in which the original sample is from a turbine or other high temperature environments are also contemplated. Although the illustrated embodiment shows the original sample passing through the humidifier 16, other embodiments in which the original sample does not pass through a humidifier (e.g., is not humidified) are also contemplated. For example, some original samples from turbines or other high temperature environments may not be humidified.

In one embodiment, the humidity of the original sample increases as the original sample passes through the fluid 22 in the humidifier 16. For example, the original sample becomes saturated with water at about 100% humidity while passing through the fluid 22 in the humidifier 16. Even if the original sample is relatively humid, the gaseous original sample is humidified to a predetermined humidity level (e.g., up to about 100% humidity) by passing through the fluid 22 in the humidifier 16. Therefore, the gaseous sample exiting the fluid 22 is referred to as a humidified sample. The humidifier 16 and the fluid 22 in the humidifier 16 act as a means for humidifying the original sample. In other embodiments, the means for humidifying the original sample may include introducing the original sample into a closed system having a predetermined humidity, and then letting the original sample equilibrate to the humidity in the closed system. The original sample is transformed into the humidified sample in the closed system. The humidified sample is then removed from the closed system.

As discussed above, the humidified sample exiting the fluid 22 is passed into the chamber 24 inside the humidifier 16. From the chamber 24, the humidified sample is fluidly communicated to an outlet 26 of the humidifier 16. The humidifier inlet 14 does not directly fluidly communicate with the humidifier outlet 26. Instead, the humidifier inlet 14 indirectly fluidly communicates with the humidifier outlet 26 via the fluid 22 in the humidifier 16.

The humidified sample exits the humidifier 16 via the humidifier outlet 26 and is fluidly communicated through a pump 30, which facilitates circulating the humidified sample through the NO sensing system 10. After passing through the pump 30, the humidified sample is fluidly communicated to a filter 32. In one embodiment, the filter 32 includes Platinum Zeolite Y filter for filtering out carbon monoxide (CO) and/or hydrocarbons. In other embodiments, it is contemplated that the filter 32 may also include Pt on other porous supports such as alumina, silica and/or other noble metals such as, for example, Pd (palladium), Rh (rhodium), Au (gold), and/or Ru (ruthenium) on porous supports.

The humidified sample is then fluidly communicated from the filter 32 to pass over the sensing element 42 situated in a heater 34. In one embodiment, the heater 34 warms the humidified sample to be within a predetermined temperature range. For example, the heater 34 heats the humidified sample to within a range of about 450° C. to about 650° C. In one embodiment, the heater 34 heats the humidified sample to about 450° C.

In the illustrated embodiment, the heater 34 is a furnace including a tube 36. In one example, the tube 36 is made of quartz. However, other embodiments, in which the tube 36 includes other materials, are also contemplated. The humidified sample is fluidly communicated from the filter 32 to an inlet 40 of the heater 34. For example, in the embodiment of the heater 34 including a tube 36, an inlet of the tube 36 acts as the heater inlet 40. Although the heater 34 is illustrated as a furnace including a tube 36, it is also contemplated that the sensing element 42 includes its own heater along with the sensors 50.

A sensing element 42 associated with the heater 34 senses an amount of NO in the humidified sample. In one embodiment, the sensing element 42 is positioned inside the heater 34. The humidified sample entering the heater 34 passes by the sensing element 42. For example, in the illustrated embodiment, the sensing element 42 is positioned inside the tube 36 in the heater 34. In this embodiment, the humidified sample is fluidly communicated from the heater (e.g., tube) inlet 40, through the tube 36 and by the sensing element 42, to an outlet 44 of the heater 34.

In the illustrated embodiment, the heater outlet 44 is an outlet of the tube 36. It is also contemplated that the heater/tube outlet 44 acts as an outlet for the system 10. The heater/tube/system outlet 44 fluidly exhausts the humidified sample to atmosphere. However, in other embodiments, it is also contemplated that the humidified sample may be captured and stored in a reservoir.

Figure 2:
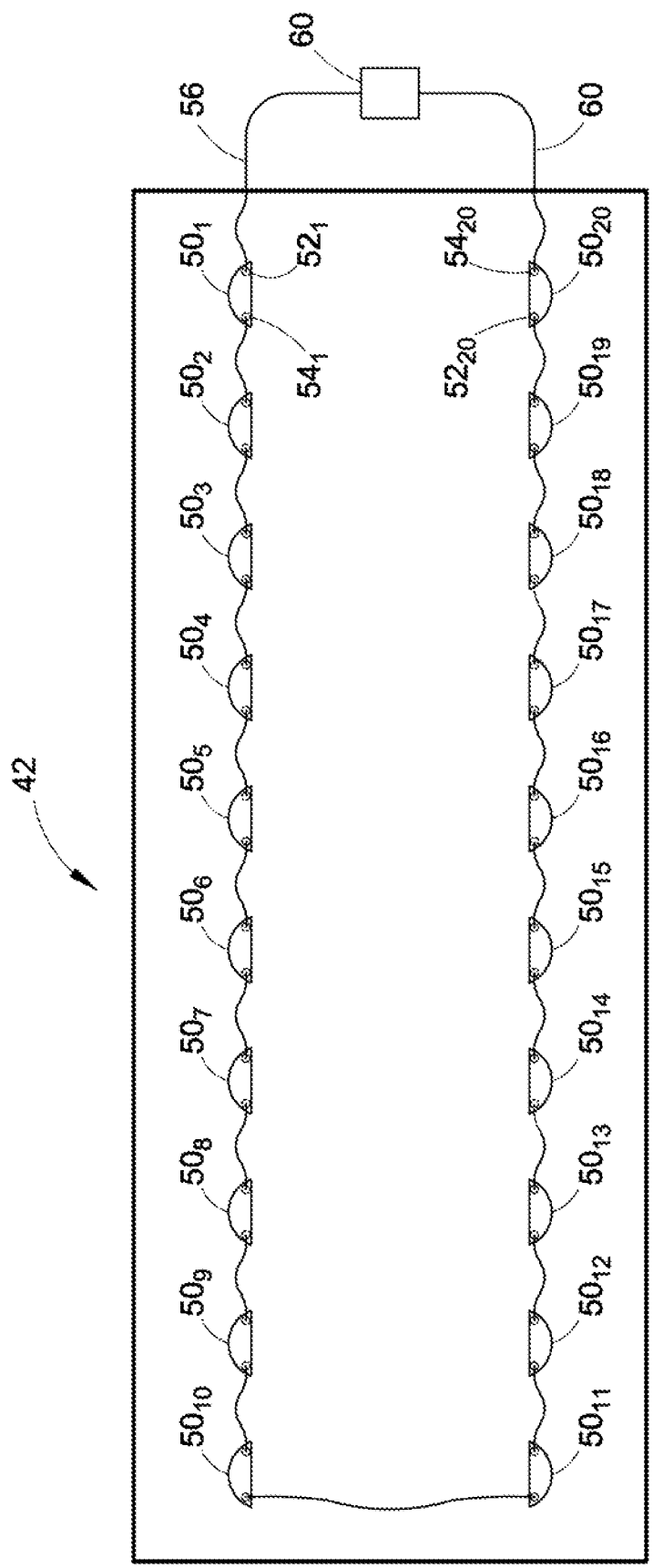
FIG. 2 illustrates a schematic representation of a sensing element including a plurality of sensors in accordance with one embodiment of an apparatus illustrating principles of the present invention.

With reference to FIG. 2, the sensing element 42 includes a plurality of sensors 50. The sensing element 42 and the sensors 50 are warmed by the heater 34 to within a range of about 450° C. to about 650° C. In one embodiment, the heater 34 warms the sensing element 42 and the sensors 50 to about 450° C. It is contemplated that the sensors 50 are solid state electrochemical sensors fabricated using yttria stabilized zirconia (YSZ), detect NO in a range of less than about 100 ppb, and are operated at a particular temperature in a range of about 450° C. to about 650° C. In one embodiment, the sensors 50 are operated at a consistent temperature of about 450° C. Once the particular temperature is set, the sensors 50 are operated consistently at that temperature for the duration of the sensing process. It is contemplated that the filter 32 operates at a different temperature (either higher or lower) than the sensors 50. For example, if the sensors 50 are operated at a consistent temperature of about 450° C., the filter 32 may be operated at a different temperature of about 250° C.

In one embodiment, the sensing element 42 includes 15 to 20 sensors 50, but any number of sensors 50 is contemplated. For example, less than 15 sensors or more than 20 sensors are contemplated. Experimental tests have shown that the sensitivity of the system 10 is based on the number of sensors 50. Generally, a system including more sensors has been found to be relatively more sensitive to NO, and a system including less sensors has been found to be relatively less sensitive to NO. More specific experimental results have shown that a system 10 including 15 sensors 50 can detect NO down to about 50 ppb; a system 10 including 20 sensors 50 can detect NO down to about 10 ppb. All of these systems can detect NO down to less than about 100 ppb. In the illustrated embodiment, the sensing element 42 includes 20 sensors $50_1$, $50_2$, $50_3$, $50_4$, $50_5$, $50_6$, $50_7$, $50_8$, $50_9$, $50_{10}$, $50_{11}$, $50_{12}$, $50_{13}$, $50_{14}$, $50_{15}$, $50_{16}$, $50_{17}$, $50_{18}$, $50_{19}$, $50_{20}$, which are collectively referenced as 50. Each of the sensors 50 generates a potential difference in response to presence of NO. It is contemplated that the potential difference generated by each of the sensors 50 is indicative of a level of NO within the humidified sample. In addition, the level of NO. within the humidified sample is indicative of a level of NO. within the original sample. Consequently, the potential difference generated by each of the sensors 50 is also indicative of a level of NO within the original sample.

Each of the sensors 50 includes a sensing electrode 52 and a reference electrode 54. For purposes of illustration, the sensing electrode 52 and the reference electrode 54 are only referenced on the first sensor $50_1$ and the twentieth sensor $50_{20}$. More specifically, the first sensor $50_1$ includes the sensing electrode $52_1$ and the reference electrode $54_1$, and the twentieth sensor $50_{20}$ includes the sensing electrode $52_{20}$ and the reference electrode $54_{20}$. A first electrical lead 56 is electrically coupled to the sensing electrode $52_1$ of the first sensor $50_1$, and a second electrical lead 60 is electrically coupled to the reference electrode $54_{20}$ of the twentieth sensor $50_{20}$. In one embodiment, the sensing electrodes 52 are $WO_3$, and the reference electrodes 54 are Pt-zeolite/Pt. However, other material for the sensing electrodes 52 and the reference electrodes 54 are also contemplated.

Each of the sensors 50 is electrically coupled to at least one adjacent sensor 50. For example, the sensors 50 are electrically connected together in series. In this series configuration, the first sensor $50_1$ is electrically connected to the second sensor $50_2$, which is electrically connected to the third sensor $50_3$, etc., until the nineteenth sensor $50_{19}$ is electrically connected to the twentieth sensor $50_{20}$. In this embodiment, the first sensor $50_1$ and twentieth sensor $50_{20}$ are only electrically connected to one (1) adjacent sensor (e.g., the second sensor $50_2$ and the nineteenth sensor $50_{19}$, respectively), while each of the other sensors $50_2$-$50_{19}$ is connected to two (2) adjacent sensors.

It is contemplated that the combined potential difference of the plurality of sensors 50 is approximately a sum of the potential differences of each of the individual sensors 50 electrically connected to one another (e.g., in series). A sensing element 42 including 15 to 20 sensors 50 has been found to generate a sum of potential differences between the plurality of sensors 50 that is capable of differentiating levels of NO in the humidified sample (and the original sample) between about 0 ppb to about 100 ppb. The combined potential difference is measurable between the first electrical lead 56 and the second electrical lead 60 via a meter 62.

Experiment

An experiment performed by the inventors is described below.

Materials

The electrochemical sensors 50 were fabricated using YSZ as solid state electrolyte. Sintered, dense, YSZ (8 mol %) rods of diameter 10 mm and length 12 cm were obtained from Ortech Advanced Ceramics (Sacramento, Calif., USA) and cut into ~1.0 mm thick semicircular discs suing a LECP VC-50 precision diameter saw (St. Joseph, Mich., USA). Pt-wire of ~0.127 mm diameter was obtained from Alfa Aesar (Ward Hill, Mass., USA). Pt-ink used for making electrode contact was obtained from Heraeus (West Conshohocken, Pa., USA). $WO_3$ powder used for making a sensing electrode was purchased from Alfa Aesar Inc. (Ward Hill, Mass., USA).

Catalytic Filter Preparation

The procedures for the fabrication of platinum loaded zeolite (Pt—Y) used as a reference electrode and filter material is as follows. Approximately 1.0 g of NaY powder (Zeolyst International) was ion-exchanged with 2.5 mM [Pt(NH3)4] Cl2 solution. The sample was dehydrated at 300° C., and then exposed to 5% $H_2$ 450° C. for 6 hours (h).

Sensor Array Fabrication

The sensor array was fabricated by adding individual sensors connected in series. The fabrication process of individual sensor unit was described above. The single sensor was made by attaching two Pt wires on a semicircular YSZ disc using a small amount of commercial Pt ink. To make the sensor array, first the semicircular YSZ discs were attached on an alumina plate with high temperature ceramic glue (Ceramabond, AREMCO product, Part No: 885). The sensor array was dried at room temperature for 4 h and cured at about 93° C., about 260° C. and about 371° C. separately for about 2 h. Sensor arrays with 2, 5, 10, 15 and 20 sensors were fabricated. All YSZ discs were connected in series with Pt wires by using a little amount of Pt-ink. Pt ink was heat treated at about 1200° C. for about 2 h to secure bonding between the Pt wire and YSZ. $WO_3$ powder was mixed with α-terpineol to form a paste, which was then painted on one of the top of Pt lead wire and calcined at about 950° C. for about 2 h to form the sensing electrode. PtY was also mixed with α-terpineol and painted on the top of the other Pt lead wire to form reference the electrode and dried at about 100° C.

Gas Sensing Measurements

Figure 3:
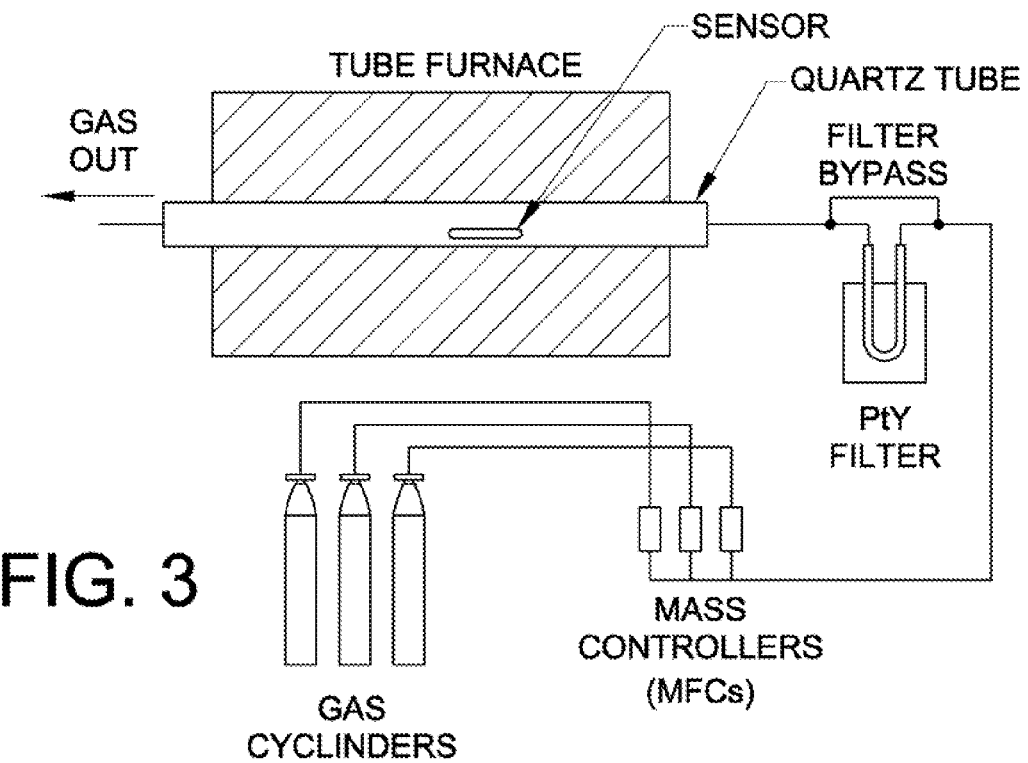
FIG. 3 illustrates a schematic diagram of an experimental setup with dry NO from certified gas cylinder.

The gas sensing experiments were performed within a quartz tube placed inside a tube furnace (Lindberg Blue, TF55035A). A computer-controlled gas delivery system with calibrated mass flow controllers (MFC) was used to introduce the test gas stream. The test gas mixtures containing different concentration of NO at constant oxygen content of 20 vol % were prepared by diluting NO (500.7 ppb NO in $N_2$) with $O_2$ and nitrogen. All gas cylinders were obtained from Praxair (Danbury, USA). The total flow rate was maintained at about 500 $cm^3$/min. A pair of Pt wires was used to connect the sensor to the external leads. The gas mixture from MFCs was introduced into the tube furnace either through or bypassing the PtY filter. The filter is a U-shape quartz tube with about 170 mg PtY placed on quartz wool. The accurate measurement of NO concentration in the parts per billion range (ppb) was independently carried out using a pre-calibrated Sievers 280i nitric oxide analyzer (GE Electronics, Boulder, Colo., USA). The electrochemical potential of the sensor array was recorded by Hewlett-Packard 34970A data acquisition system with about 10 MΩ and about 10 GΩ internal impedance. The sensor array was tested over the temperature range of about 400° C. to about 600° C. FIG. 3 shows a schematic of the setup.

Breath Analysis Experiment

Figure 4:
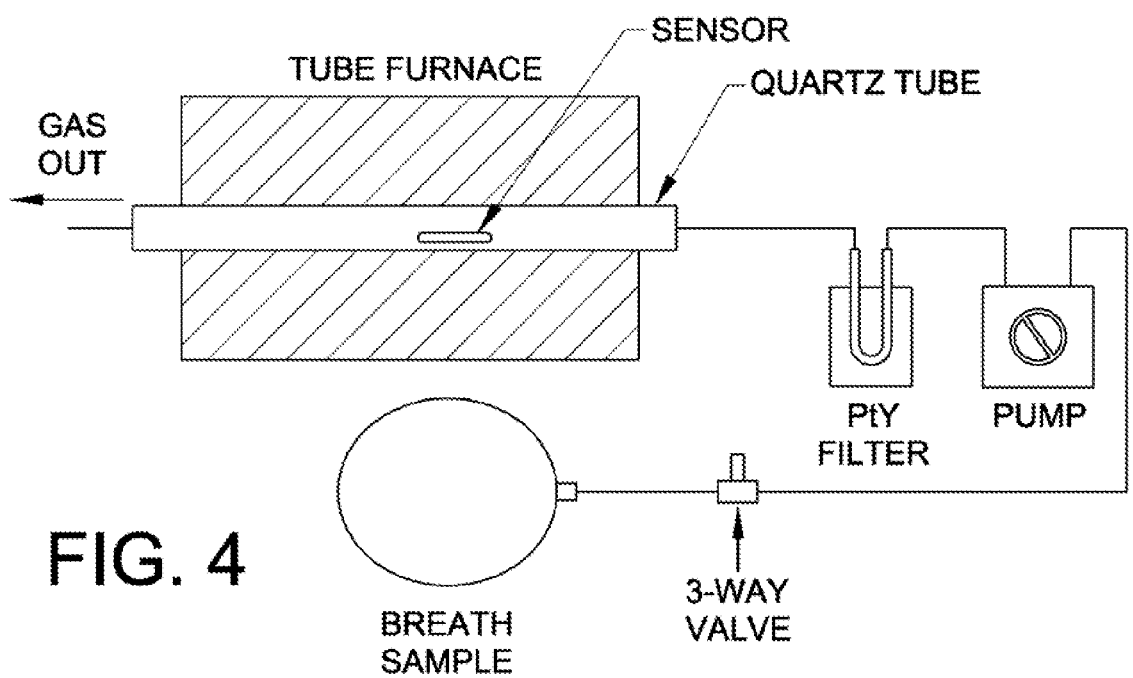
FIG. 4 illustrates a schematic diagram of an experimental setup with a breath sample without a moisture trap.
Figure 5:
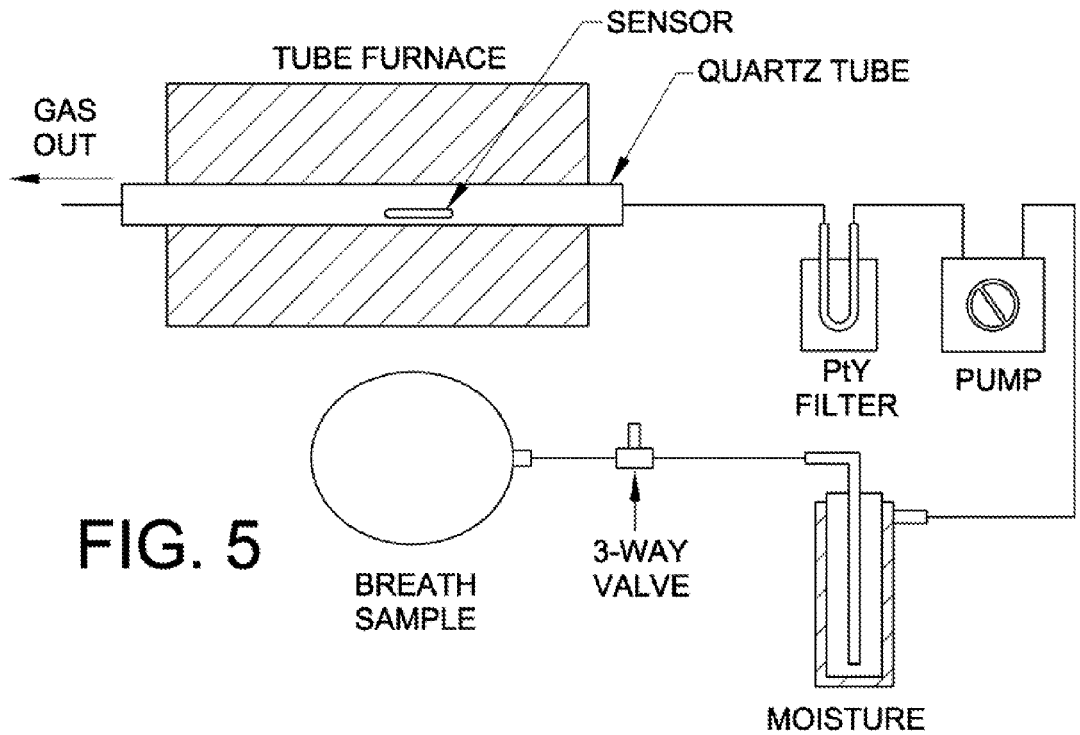
FIG. 5 illustrates a schematic diagram of an experimental setup with a breath sample using a moisture trap of dry ice/acetone.
Figure 6:
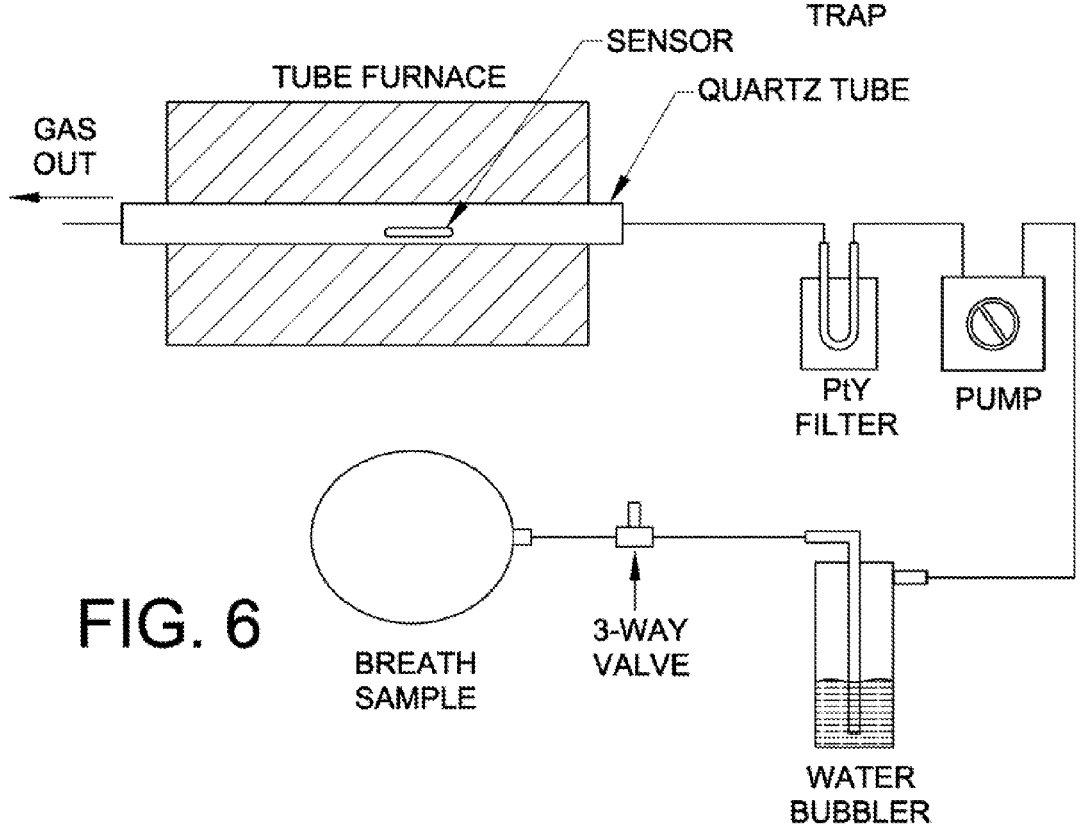
FIG. 6 illustrates a schematic diagram of an experimental setup with a breath sample with a water bubbler.

The breath analysis experiment was performed in three different configurations, as shown in FIGS. 4-6. Exhaled breath samples were collected from volunteers into a respective Mylar sampling bags, using protocols practiced in the clinical field. The NO concentration in the breath sample was then measured with a Sievers instrument. For all volunteers, the amount of NO was less than about 10 ppb. In order to establish calibration curves, it was necessary to get NO at higher concentrations, and this was done by spiking the breath samples in the Mylar bags with bottled NO, and the total amount introduced was measured with the Sievers unit. The concentration ranges examined were between about 5 ppb and about 80 ppb NO in breath. The Mylar bags were re-used and thoroughly cleaned before each use with flowing nitrogen (99.998% purity) gas. Instead of mass flow controllers, a pump (Hargraves Technology Corporation, Mooresville, N.C., USA) was used to maintain a constant flow rate of about 500 cm$^3$/min. In the first series of experiments (FIG. 4), the breath sample followed the same path through the Pt—Y filter as with the dry bottled gases. In the second series (FIG. 5), the breath sample was passed through a dry ice/acetone-slurry trap to remove the moisture from the collected breath. The inlet of the dry ice trap was connected with a three way valve which allows either breath sample or ambient air. In the third series (FIG. 6), the breath sample and the ambient air was bubbled through water at room temperature, and no dry ice trap was used.

Results of Experiment

Assembly of Sensor Array

Figure 7:
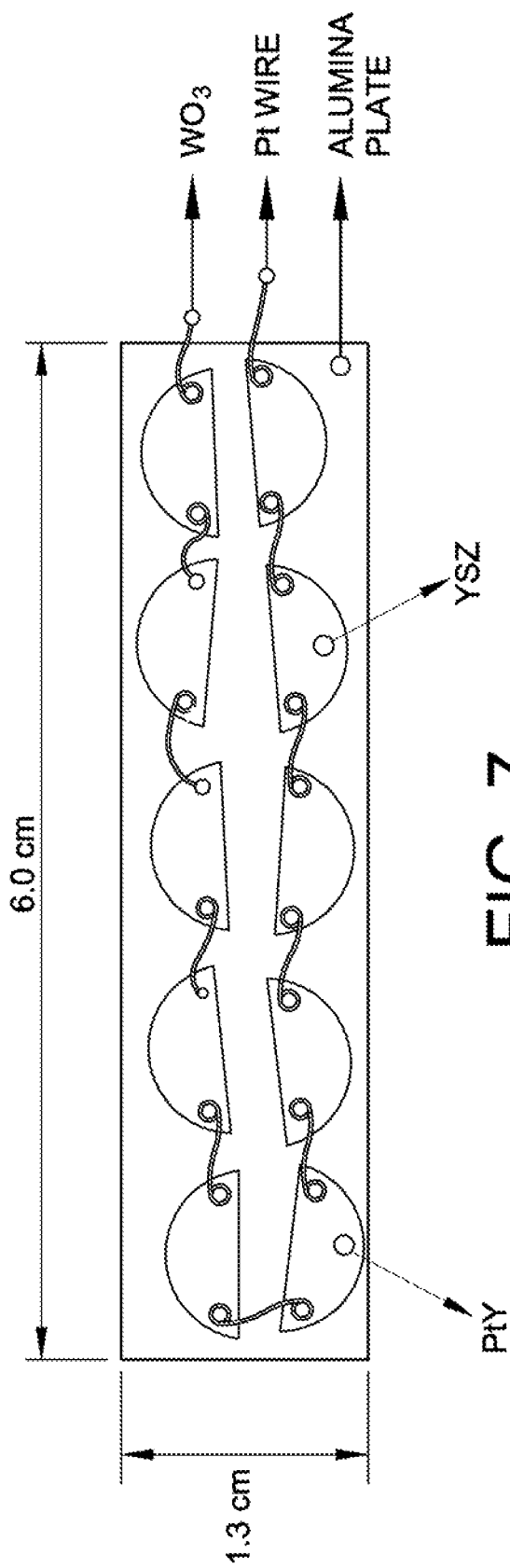
FIG. 7 illustrates a 10 NO sensor array.

The basic unit of the sensor is sintered YSZ with a $WO_3$ sensing electrode and Pt-zeolite Y (PtY) reference electrode coated on a Pt lead wire. In this study, we have investigated 2, 5, 10, 15 and 20-sensors connected in series. FIG. 7 shows a photograph of a 10-sensor array. Each hemispherical disk is YSZ with $WO_3$ (yellow) and PtY/Pt (black) electrodes connected in series, and mounted on an alumina plate. The dimension of the 10-sensor array was about 1.3 cm×about 6.0 cm.

Sensing Response to NO

Figure 8:
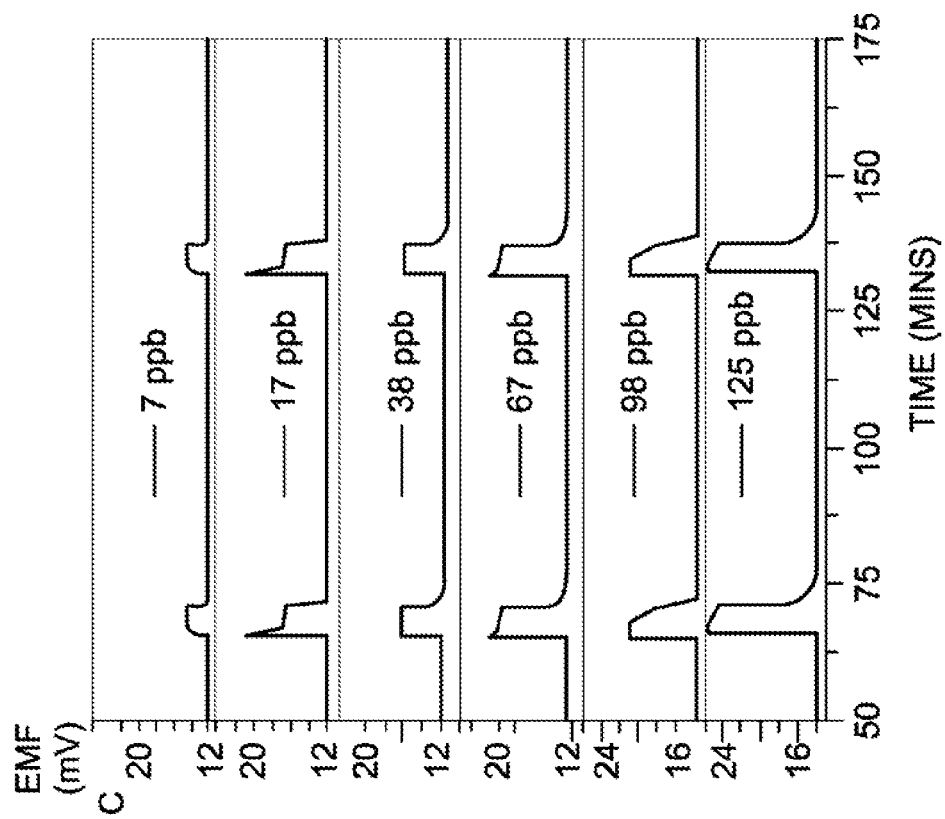
FIG. 8 illustrates a sensor response of a 2-NO sensor array with 7-125 ppb NO without PtY filter. The sensor was tested at about 600° C., about 20% $O_2$ and about 500 cm³/min total flow rate.
Figure 9:
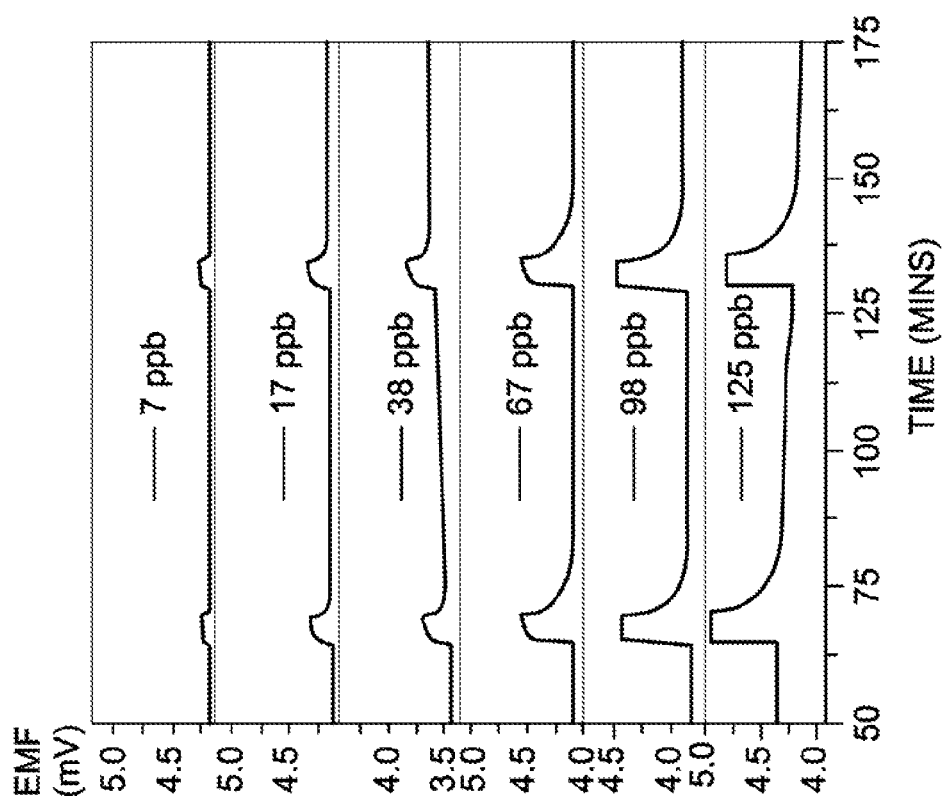
FIG. 9 illustrates a sensor response of a 10-NO sensor array with 7-125 ppb NO without PtY filter. The sensor was tested at about 600° C., about 20% $O_2$ and about 500 cm³/min total flow rate.
Figure 10:
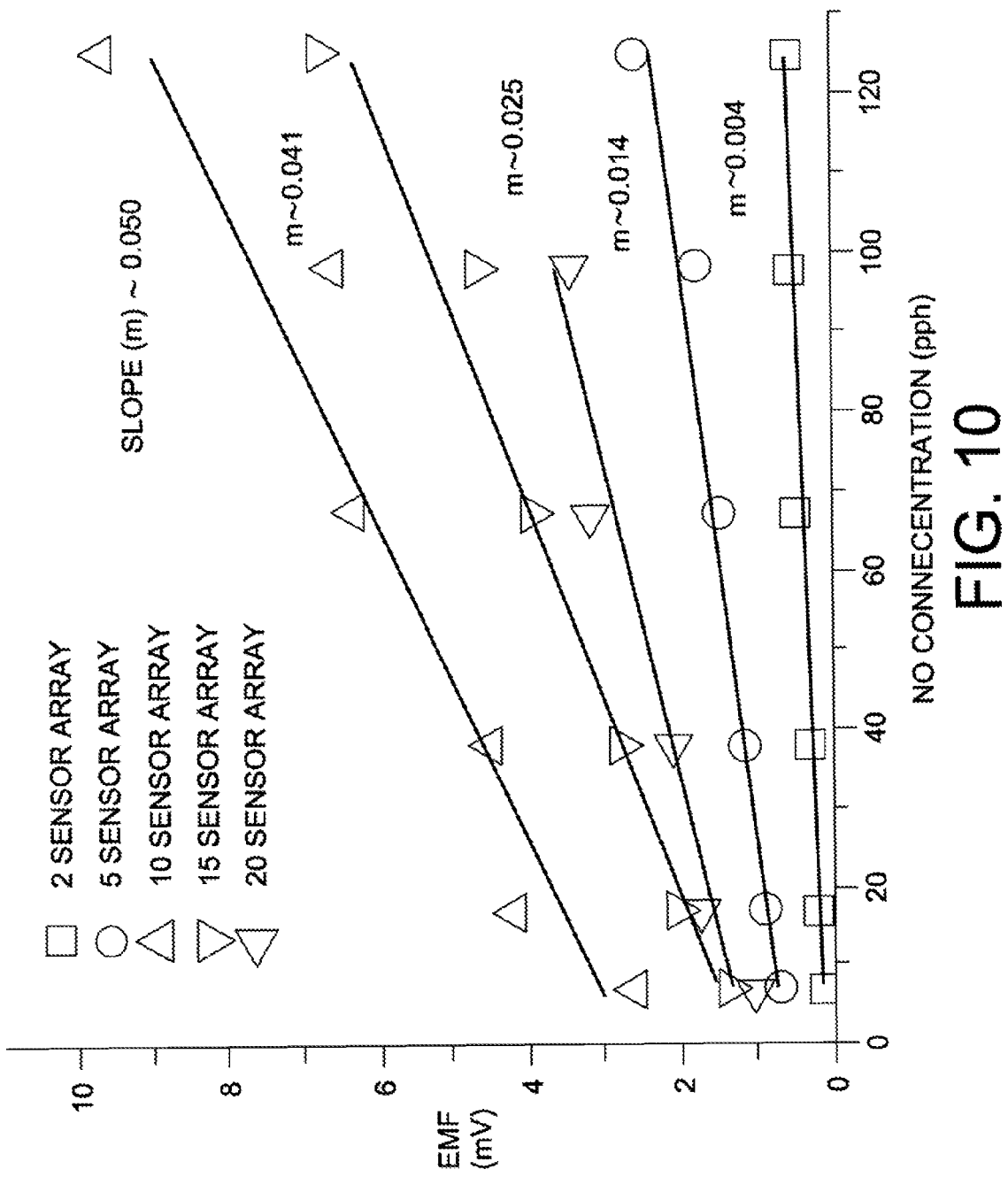
FIG. 10 illustrates a change in EMF with NO concentrations for 2, 5, 10, 15 and 20 sensor array with about 10 MΩ, internal resistance on the multimeter. The sensors were tested at about 600° C. with about 20% $O_2$, total flow rate about 500 cm³/min.
Figure 11:
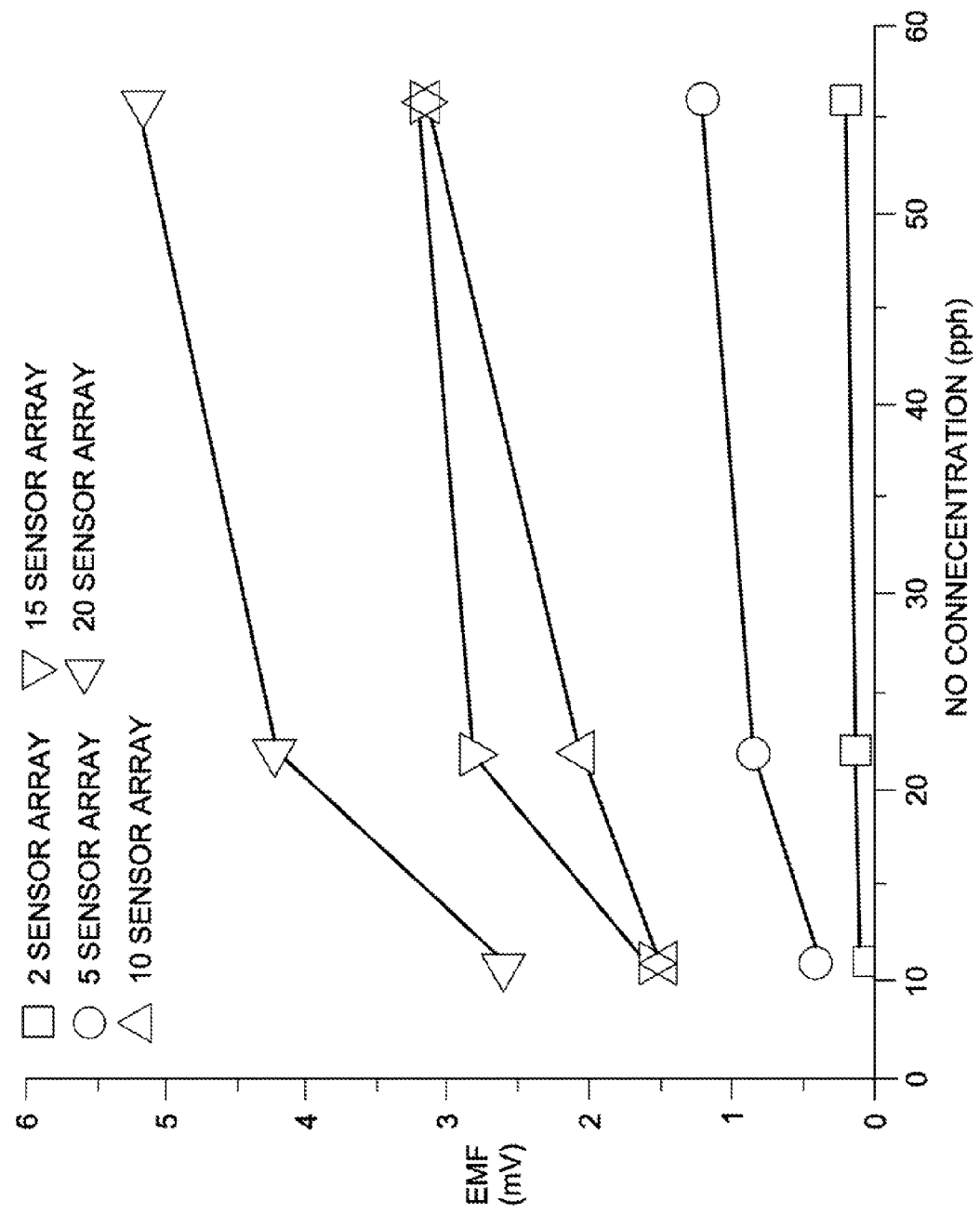
FIG. 11 illustrates a change in EMF with NO concentrations for 2, 5, 10, 15 and 20 sensor array with about 10 GΩ internal resistance on the multimeter. The sensors were tested at about 600° C. with about 20% $O_2$, total flow rate about 500 cm³/min.

The sensing response of a 2-sensor and 10-sensor array to dry NO (bottled gas) in the range of about 7 ppb to about 125 ppb is shown in FIGS. 8 and 9 (the y-axis EMF value is the same for each individual plot in the figure, so the responses can be compared). The sensors were maintained at a temperature of about 600° C. in a background gas of about 20% $O_2/N_2$. It is clear that there is a significant increase in EMF for each array with the NO concentration, as well as a higher response with the 10-sensor array as compared to the 2-sensor array (e.g. with 7 ppb NO, the 2-sensor array produced a response of ~0.2 mV as compared to ~2.5 mV for the 10-sensor array). These experiments were then repeated with the 5, 15 and 20 sensor array and the change in EMF is plotted against the NO concentration in FIG. 10. The slopes increase, as expected on going from 2 to 5 to 10 sensor array, but then drops off unexpectedly for 15- and 20-sensor arrays. The bulk resistances of the arrays were measured at about 600° C. and found to be 1, 3.5, 6.3 and about 17 MΩ for the 5, 10, 15 and 20-sensor array. We reasoned that the internal impedance of the multimeter (10 MΩ) was not appropriate for the measurements of these high resistance arrays. Thus, the experiments were all repeated with a multimeter with a about 10 GΩ internal impedance and these data are shown in FIG. 11. Over the about 10 ppb to about 60 ppb range, the sensors behaved appropriately, with the larger arrays producing relatively stronger signals. Henceforth, all the data shown is with the about 10 GΩ internal impedance multimeter.

Removal of Interfering Gases

Figure 12:
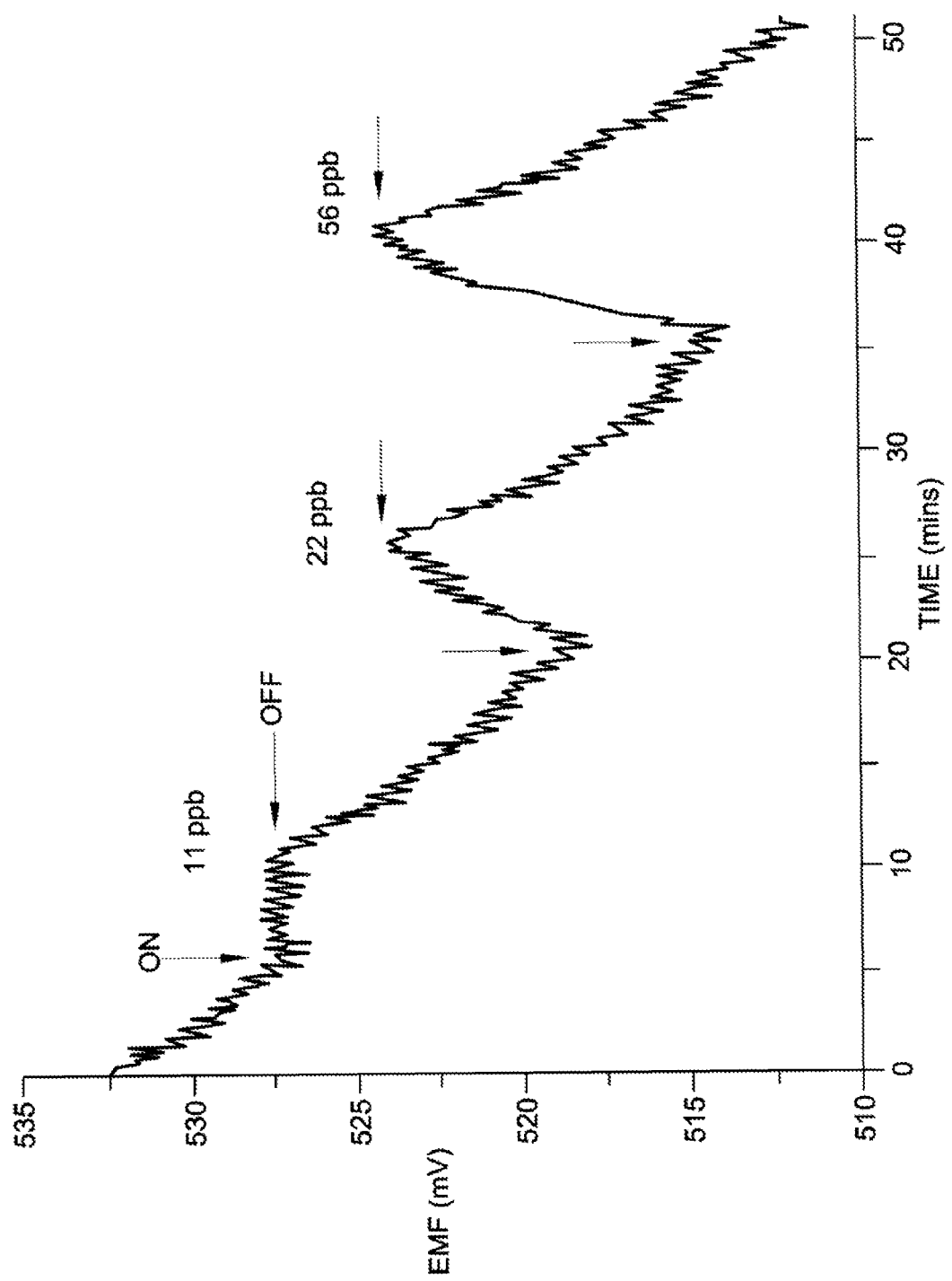
FIG. 12 illustrates response transients to about 11 ppb to about 56 ppb NO for a 10 sensor array without the NO gas passing through the catalytic PtY filter. The sensor was tested at about 425° C., PtY filter at about 250° C., about 20% $O_2$ and a total flow rate about 500 cm³/min.
Figure 13:
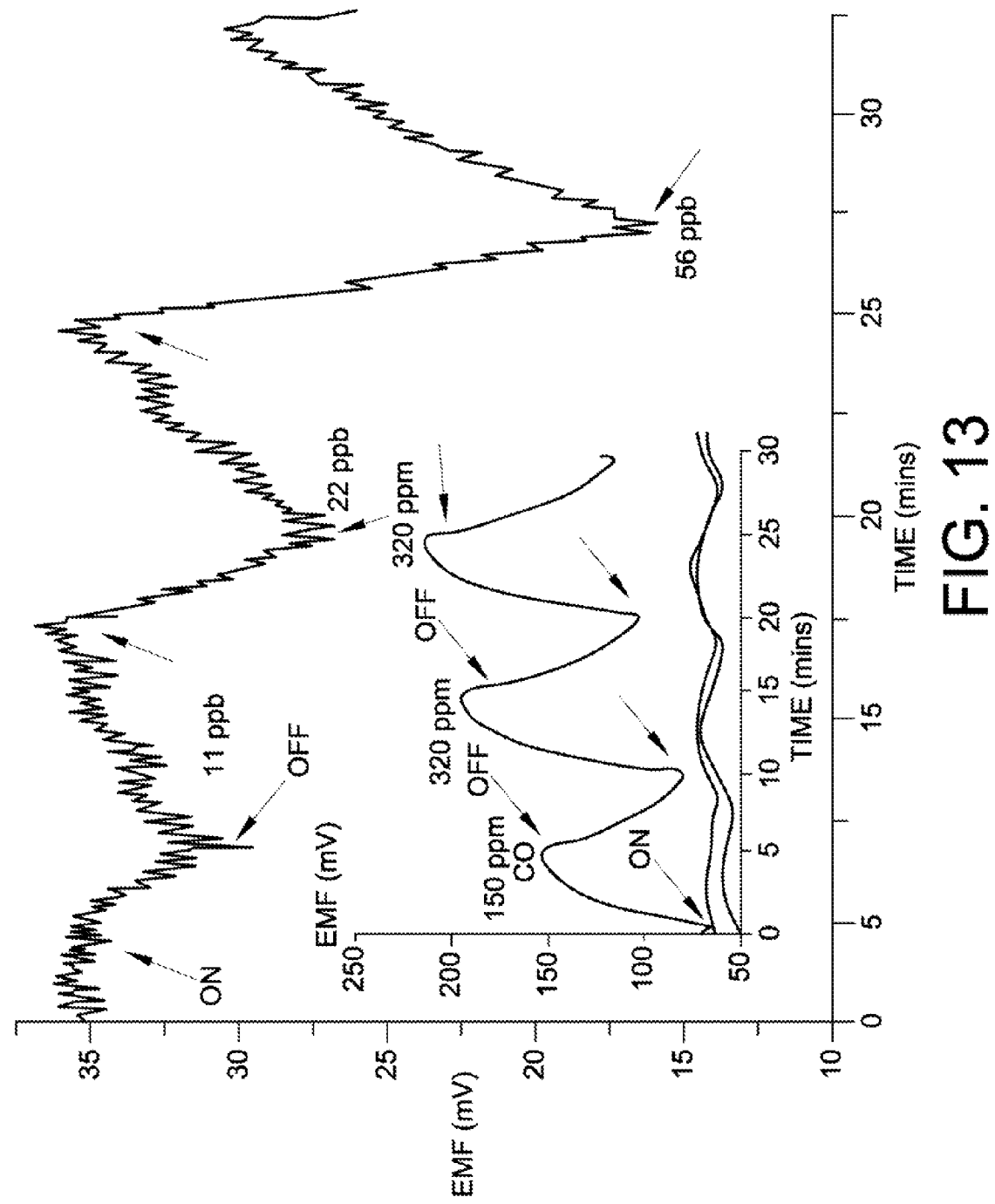
FIG. 13 illustrates response transients to about 11 ppb to about 56 ppb NO for a 10 sensor array with the NO gas passing through the catalytic PtY filter. The sensor was tested at about 425° C., PtY filter at about 250° C., about 20% $O_2$ and a total flow rate about 500 cm³/min. Inset illustrates response transients to about 160 ppm to about 320 ppm CO with and without the PtY filter at about 200° C. and about 250° C.

We investigated the operation of the 10-sensor array at various temperatures (e.g., about 400° C. to about 600° C.), with the goal of establishing the lowest operational temperature. This was motivated by the fact that a practical embodiment of this device should use the lowest possible temperature in order to minimize the power load. The data at about 425° C. had appropriate response and recovery time of minutes, and the data for the 10-sensor array is shown in FIG. 12. Adequate EMF changes were observed for NO in the about 11 ppb to about 56 ppb range (2-12 mV), though the response/recovery times were slower. Potentiometric NO sensors show strong interference to hydrocarbons and CO. Considering that breath samples have oxidizable gases at much higher concentrations (factor of about 1000) than NO, in one embodiment these gases were removed prior to NO detection. Similar interferences can also be expected in combustion systems. One approach that we have demonstrated previously is the use of a Pt-zeolite catalyst. In an embodiment where the catalyst is maintained at a temperature different from the sensor, a total NO response is observed. The schematic of this apparatus is shown in FIG. 3. To model the interference, we chose CO. The inset in FIG. 13 shows that about 160 ppm to about 320 ppm CO (no NO in the gas stream) produces a relatively very strong response with the 10-sensor array at about 425° C. However, if the CO is passed through a Pt-zeolite Y fitter at about 200° C. or about 250° C., the response to CO is minimized (the wavy baseline is not due to sensor responding to CO, since the rise and crest of the wave does not coincide with gas introduction or shut off).

The response to only NO after it passes through the filter is shown in FIG. 13, and the signal is in the opposite direction, as compared to comparable NO concentrations that do not pass through the filter (FIG. 12). The reason for this reversal in signal is that the filter converts the NO to $NO_2$ with almost 98% efficiency at temperatures of about 200° C. to about 250° C. Signal from $NO_2$ is reversed as compared to NO($NO_2$+ 2e→$O^2$—+NO) Also, the signal is considerably stronger (about 5 mV to about 20 mV for the about 11 ppb to about 56 ppb NO passing through the filter) as compared to NO not passing through the filter (FIG. 12). The relatively stronger signal with the $NO_2$ arises from the greater driving force for the reduction reaction at higher temperatures, since NO is the more stable product with increasing temperatures. All further experiments were carried out with the filter-sensor combination.

Breath Analysis

Figure 14:
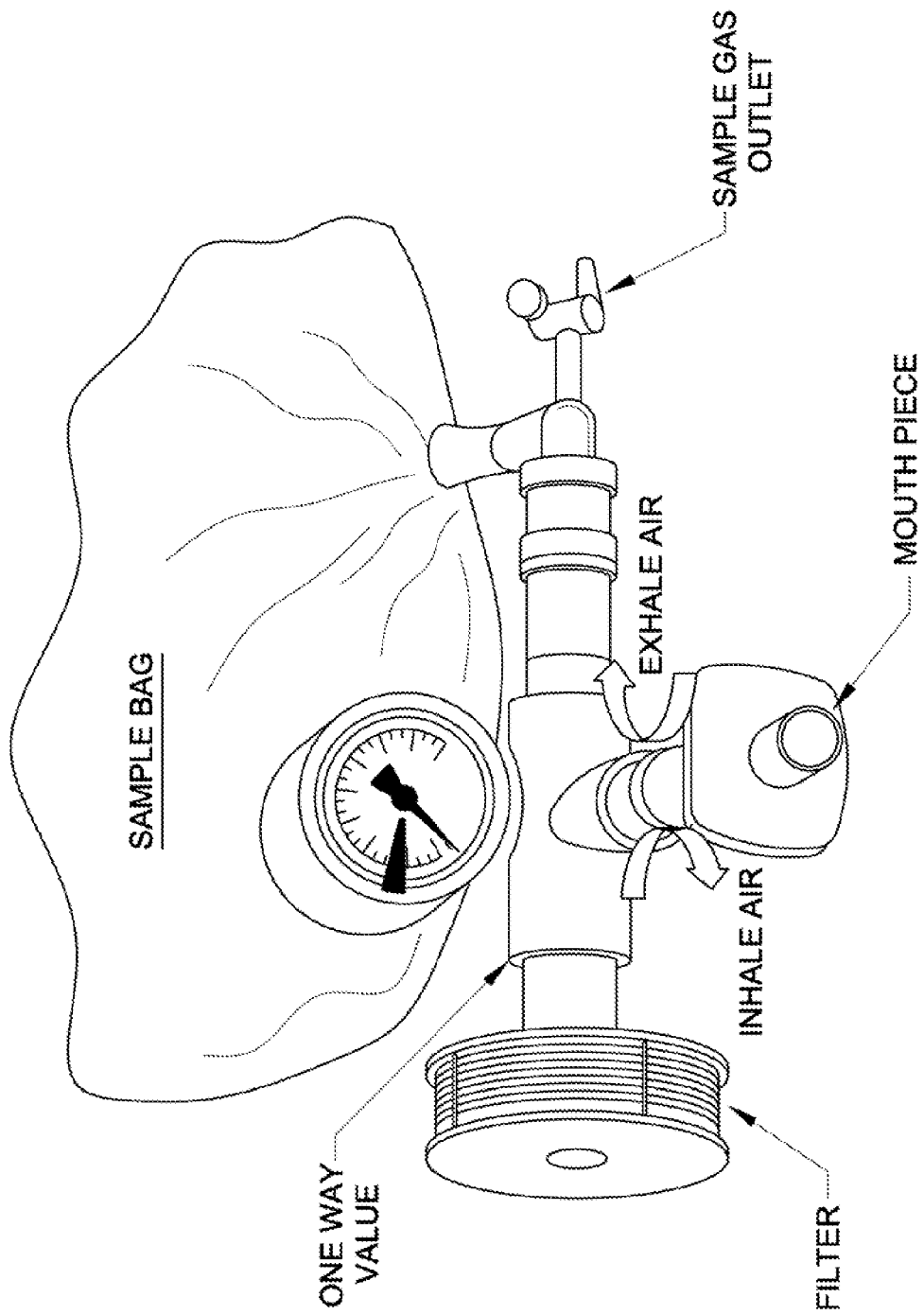
FIG. 14 illustrates breath collection setup equipment.

For breath analysis, the measurement configuration was altered, and shown schematically in FIGS. 4-6. Breath samples from human volunteers were collected in a bag, shown in FIG. 14. The level of NO in the bag was determined with the Sievers chemiluminescence analyzer and for all volunteers was found to be less than about 10 ppb. Thus, to establish the capability of the sensor system it was necessary to get higher concentrations of NO into the bag. This was done by introducing small amounts of bottled NO into the bag containing the human breath (ppb), and the exact level of NO in the bag was measured using the Sievers analyzer.

Figure 15:
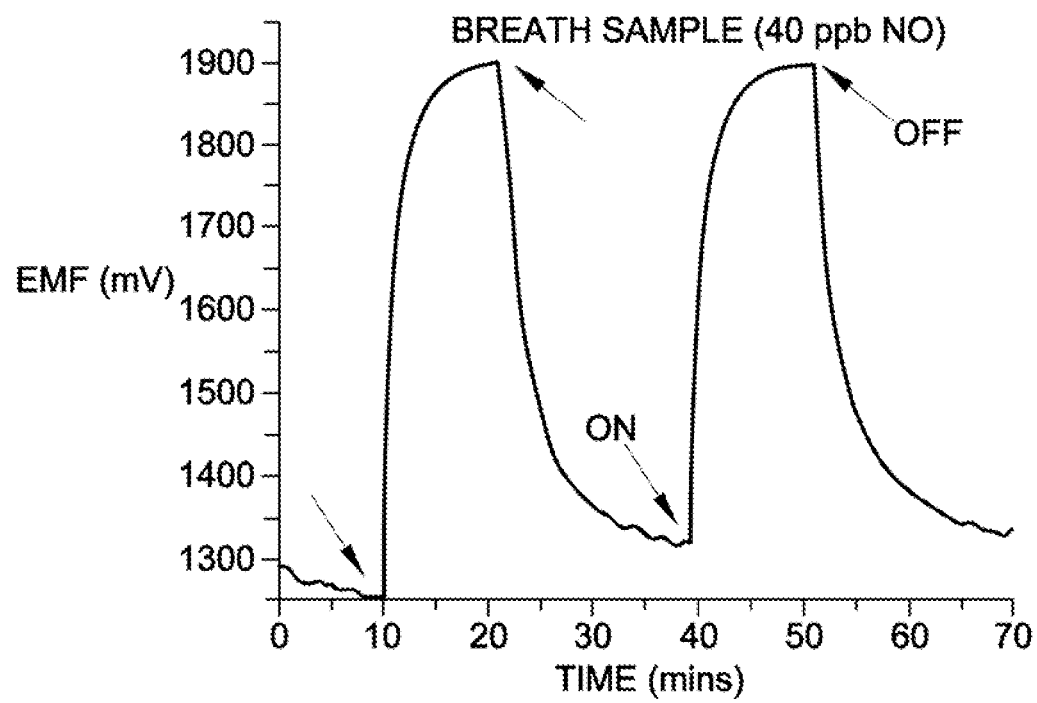
FIG. 15 illustrates a sensor response with breath sample (~40 ppb NO) for a 10-sensor array bypassing a PtY filter at about 250° C. Sample at about 425° C. and about 500 cm³/min constant flow rate was maintained using a pump.
Figure 16:
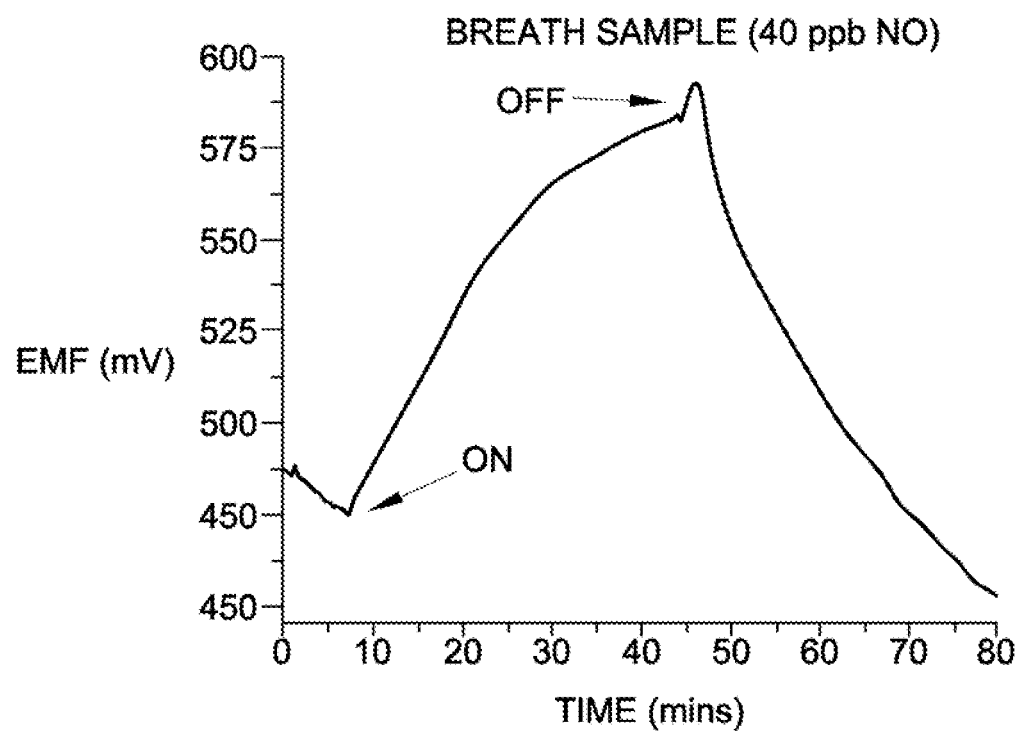
FIG. 16 illustrates a sensor response with breath sample (~40 ppb NO) for a 10-sensor array with a PtY filter at about 250° C. Sample at about 425° C. and about 500 cm³/min constant flow rate was maintained using a pump.

FIGS. 15 and 16 show the data with a 10-sensor at about 425° C. for an about 40 ppb NO breath sample with the gas either bypassing (FIG. 15) the Pt—Y filter or through (FIG. 16) the filter maintained at about 250° C. It is immediately obvious from FIG. 15 that the signal observed (~600 mV) far exceeds what is expected from about 40 ppb NO (~10 mV, FIG. 12). Upon passing this breath sample through the filter, the signal should have reversed (from $NO_2$, FIG. 13), but we still observe a NO-like signal of ~100 mV. Passing through the filter does decrease the interference, but does not eliminate them. This filter is primarily good at removing interferences from oxidizable gases, such as CO and hydrocarbons. Clearly, there are components in breath that are producing strong interferences and overwhelming the NO signal. Since the breath sample is almost 100% water, our hypothesis was that the interference arises primarily from water. Indeed, bubbling dry NO gas through water gave signals comparable to FIG. 15 (data not shown).

Figure 17:
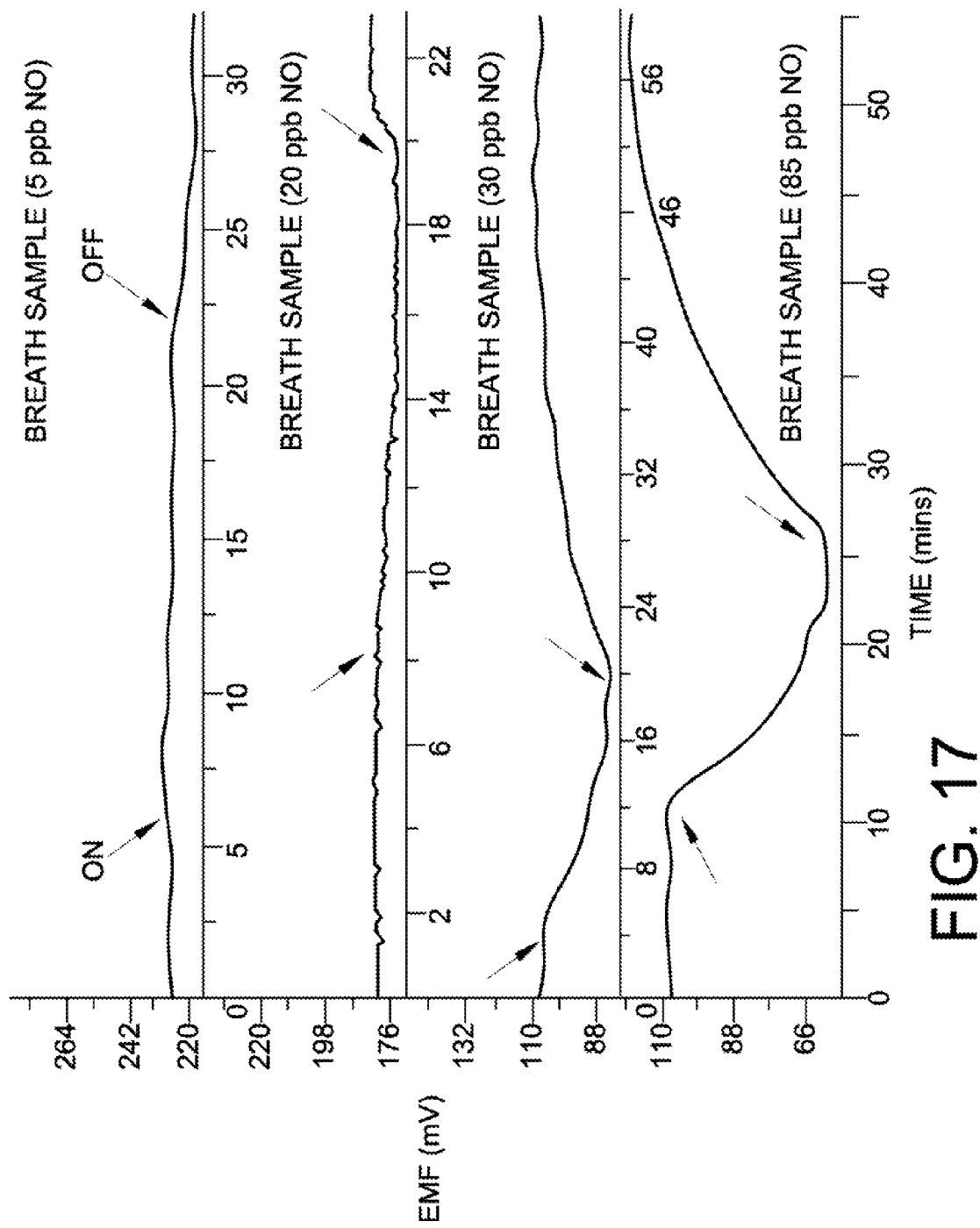
FIG. 17 illustrates response transients with breath samples for a 10 sensor array. The samples were tested at about 425° C., PtY filter at about 250° C. and using moisture (dry ice) trap.
Figure 18:
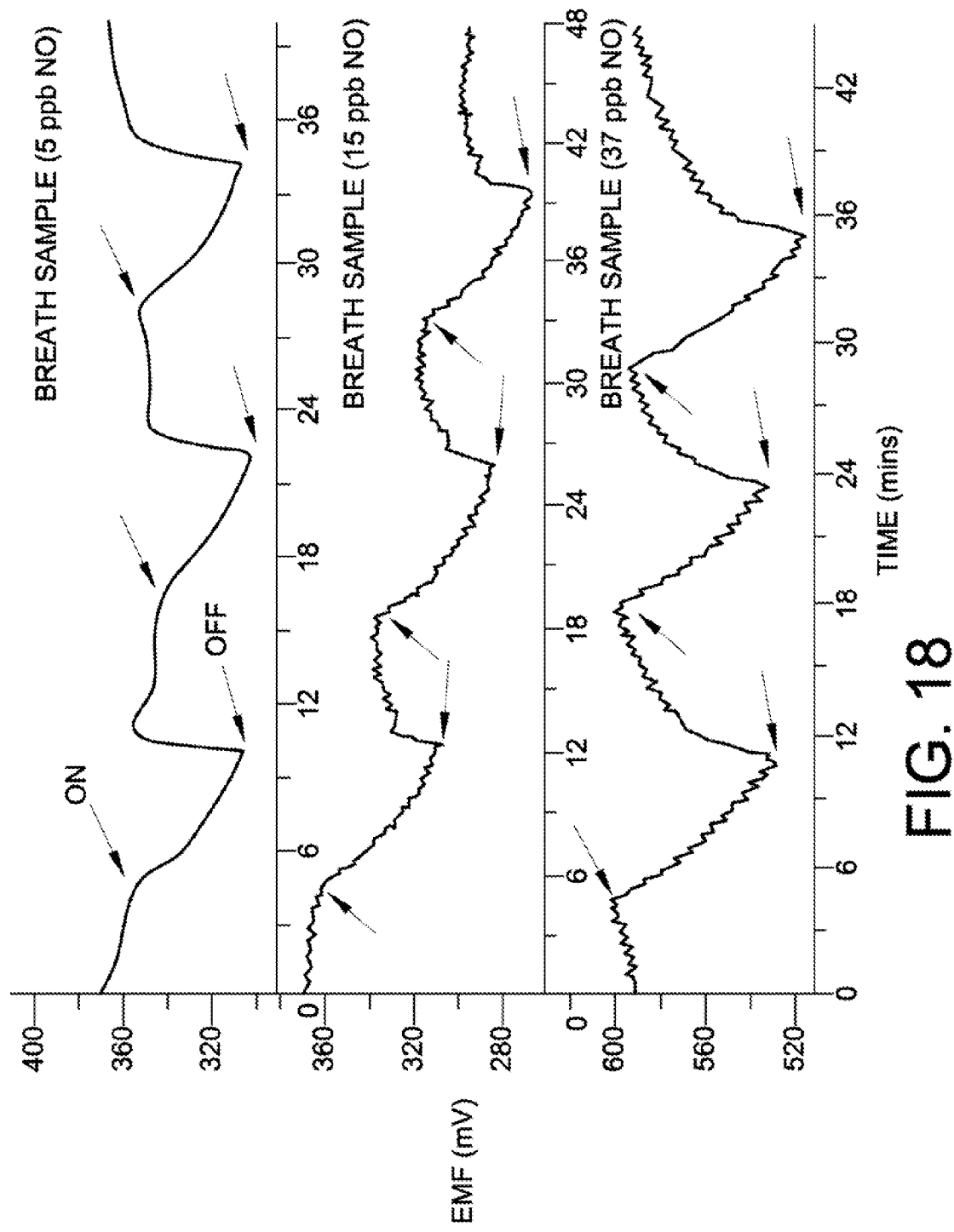
FIG. 18 illustrates response transients with breath samples for a 20 sensor array. The samples were tested at about 425° C., PtY filter at about 250° C. and using moisture (dry ice) trap.

We considered that the most effective way to remove the water interference was to pass the breath through a dry ice/acetone slurry trap maintained at about −78° C., as shown schematically in FIG. 5. Considering that the boiling point of NO is −158.8° C., none of the NO is expected to be trapped and the vapor should be completely water free. FIG. 17 shows the response of a 10-sensor array to about 5 ppb, about 20 ppb, about 30 ppb, and about 85 ppb NO in breath sample (all on the same y-axis scale). The 10-sensor array does not respond to about 5 ppb NO, and barely to about 20 ppb NO, but higher concentrations are readily detected. In order to increase the sensitivity to the low ppb NO, breath samples were analyzed with a 20-sensor array, and results for about 8 ppb, about 15 ppb, and 37 ppb are shown in FIG. 18. Increasing the number of sensors brings the detection limits of the sensor array to levels appropriate for clinical analysis. However, to achieve this low ppb sensitivity, it was essential to remove all of the $H_2O$ from the breath stream. The choice of a dry ice bath, though accomplishing the goal of water removal will be difficult in practice, so alternative strategies were explored.

Figure 19:
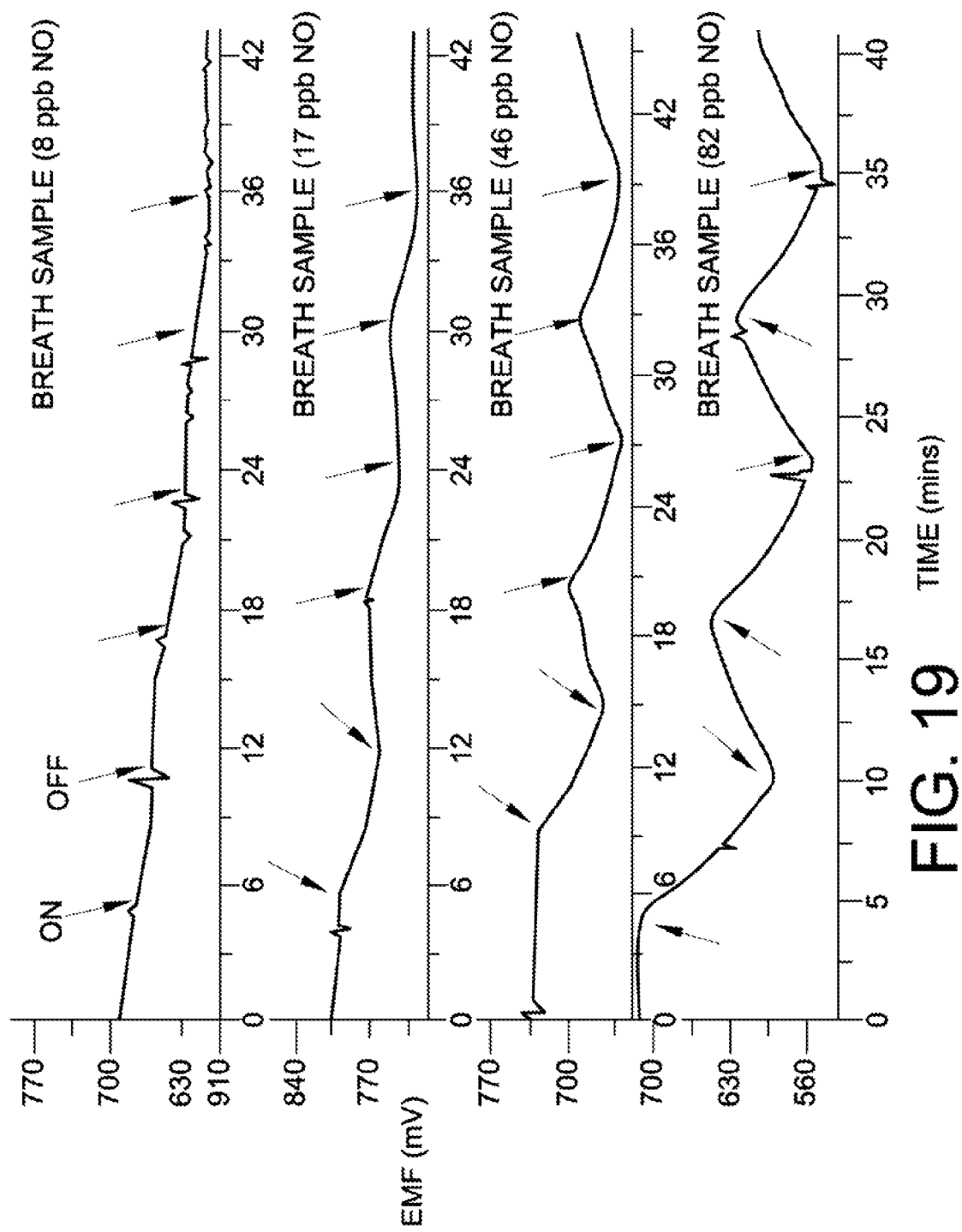
FIG. 19 illustrates response transients to about 8 ppb to about 82 ppb breath sample for a 20 sensor array. The signals were measured by passing breath samples as well as reference air through water.
Figure 20:
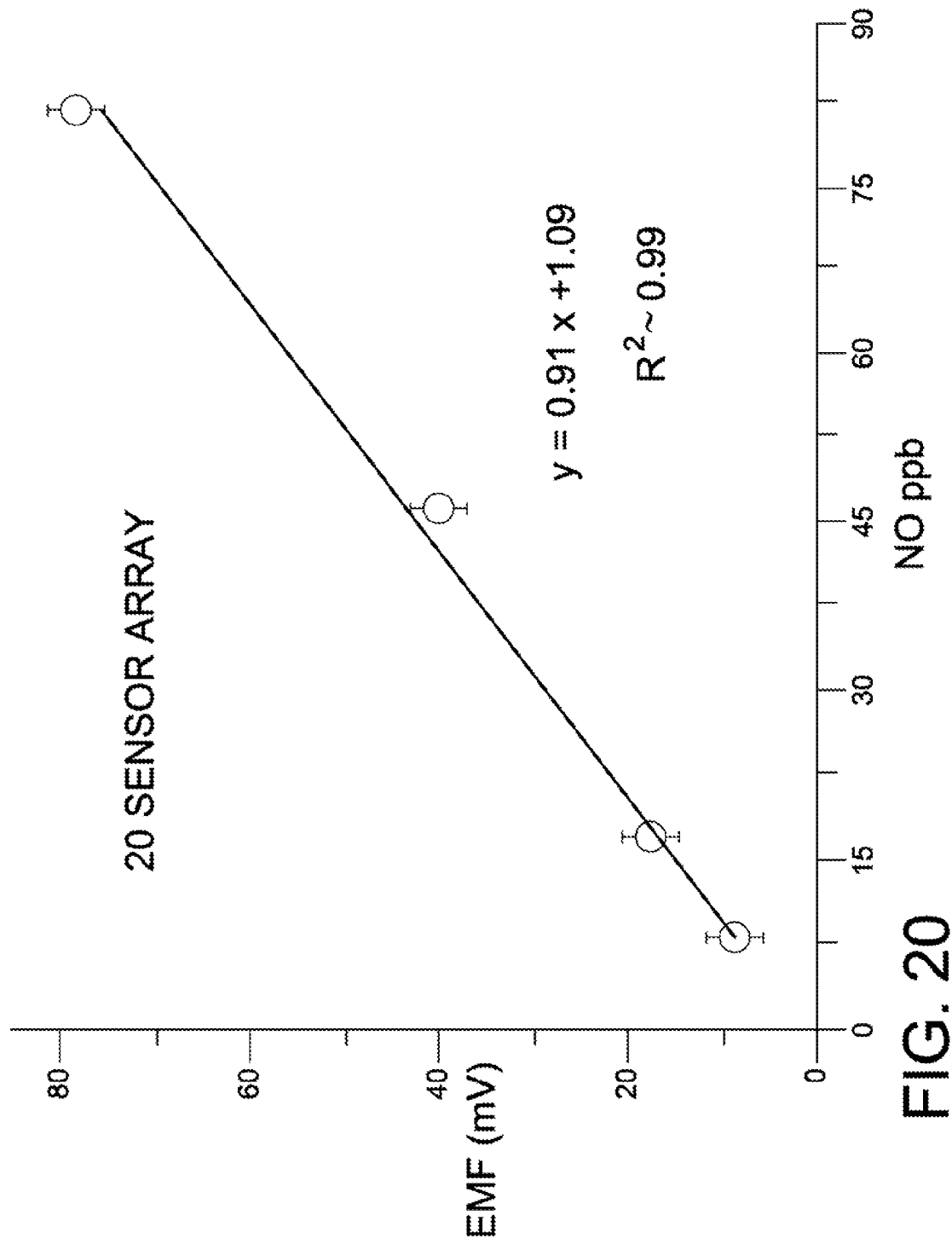
FIG. 20 illustrates variation of EMF with different NO concentrations in breath. The sample was at about 425° C. and the PtY filter was at about 250° C.

As is seen in FIGS. 15 and 16, there is a large change in signal upon exposing the sensor array to water, and this signal is stable as long as water is in the gas stream. So, a strategy was to use humid air as the background gas. The experiment involved saturating both the background air and the breath sample by bubbling through water, prior to exposure to the sensor (FIG. 6). These data for a 20-sensor array are shown in FIG. 19, for about 8 ppb, about 17 ppb, about 46 ppb, and about 82 ppb NO. Clearly, this is a workable strategy and does not need removal of the water, but just ensuring the background gas and the breath stream are both water saturated. FIG. 20 shows the calibration curve for the 20-sensor array over the range relevant for clinical analysis.

Discussion of Experiment

The particular sensor unit used in the arrays in this paper has been studied extensively. The choice of $WO_3$ as sensing electrode and PtY/Pt as the reference electrode is based on their chemical reactivity for NO equilibration, with $WO_3$ being relatively poor and PtY/Pt relatively more efficient. Other studies have also examined the advantages of $WO_3$ as a sensing electrode for potentiometric sensors.

All of the data with the sensor arrays (FIGS. 8, 9, and 17-20) demonstrates the concept of increasing sensitivity by combining potentiometric sensors in series. This concept has been reported earlier with potentiometric oxygen sensors. However, with increase in the number of sensors, the resistance of the device also increases, and the measurement needs to be carried out with appropriate high impedance instruments.

For measuring relatively dry NO in the ppb range, 10-sensor array was adequate (FIGS. 12 and 13). Interferences such as CO, hydrocarbons can be removed with a catalytic filter, as long as the filter temperature is maintained at a different value as compared to the sensor. Our relevant data was obtained with the catalytic filter at about 250° C. and sensor at about 425° C. Such devices can be used for measuring low levels of NO in combustion environments, as generated in turbine engines.

However, measuring NO in breath samples was more difficult, primarily due to the high water content. We have presented two strategies for negating the effect of water. The first one was by freezing the water out by passing the breath through a dry ice bath. Combining the bath with the catalytic filter, we were able to get reasonable signals for NO in breath at concentrations relevant for clinical analysis (e.g., about 1 ppb to about 100 ppb), but it required the use of a 20-sensor array. The second more practical strategy of minimizing the water effect was to use water saturated air as the background gas. Both these water neutralization strategies resulted in calibration curves for NO with similar slopes, and provide confidence in the measurement techniques.

Calibration curves with analyte gas usually show algorithmic relationships to gas concentration for mixed potential sensors, whereas the calibration curve in FIG. 20 shows a linear dependence (R2=99%). Previous studies with CO in air with potentiometric sensors have also shown a linear dependence at low concentrations and explained with the help of mass transport considerations. An added advantage of measuring the low concentrations is therefore the linearity of the calibration curve, making clinical analysis more convenient.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicant's general inventive concept.

We claim:

1. An NO sensing system for measuring NO in a breath sample, the system comprising:
    an inlet configured to receive the breath sample as it is exhaled by a subject;
    a humidifier fluidly communicating with the inlet and configured to humidify the breath sample as it transmits the breath sample through the humidifier to a humidifier outlet, such that the breath sample exits the humidifier outlet as a humidified sample having a humidity above a predetermined level; and
    a sensing element comprising a plurality of sensors electrically coupled together, each of the plurality of sensors configured to generate a potential difference in response to presence of NO in the humidified sample;
    wherein the plurality of sensors comprises an effective number of sensors coupled together such that a combined potential difference of the plurality of sensors can indicate a level of NO less than about 100 ppb in the breath sample.

2. The NO sensing system as set forth in claim 1, wherein the humidified sample has a humidity of about 100%.

3. The NO sensing system as set forth in claim 1, wherein the combined potential difference of the plurality of sensors includes a sum of the potential differences of each of the plurality of sensors.

4. The NO sensing system as set forth in claim 3, wherein the plurality of sensors comprises at least 15 sensors.

5. The NO sensing system as set forth in claim 4, wherein the sum of the potential differences of the at least 15 sensors is capable of indicating a level of NO down to about 10 ppb in the breath sample.

6. The NO sensing system as set forth in claim 1, wherein the plurality of sensors are electrically connected together in series.

7. The NO sensing system as set forth in claim 6, wherein each of the plurality of sensors includes a sensing electrode and a reference electrode,
    wherein the sensing element further comprises:
        a first electrical lead electrically coupled to the sensing electrode of a first sensor of the plurality of sensors electrically connected together in series;
        a second electrical lead electrically coupled to the reference electrode of a last sensor of the plurality of sensors electrically connected together in series; and
    wherein the combined potential difference of the plurality of sensors is measurable between the first and second electrical leads.

8. The NO sensing system as set forth in claim 1, wherein the system further comprises a heater warming the plurality of sensors.

9. The NO sensing system as set forth in claim 1, wherein the humidifier includes a humidifier inlet configured to direct the breath sample into a liquid fluid; such that the breath sample passes through the liquid fluid and exits the liquid fluid as the humidified sample.

10. The NO sensing system as set forth in claim 9, wherein passing through the liquid fluid comprises bubbling through the liquid fluid.

11. The NO sensing system as set forth in claim 1, wherein the plurality of sensors comprises at least 8 sensors.

12. A method of sensing NO in a breath sample, the method comprising:
    receiving a breath sample from a subject;
    humidifying the breath sample into a humidified sample having a humidity above a predetermined level; and
    contacting a sensing element with the humidified sample, wherein the sensing element comprises a plurality of sensors electrically coupled together, thereby generating a combined potential difference of the plurality of sensors in response to presence of NO in the humidified sample;
    wherein the plurality of sensors comprises an effective number of sensors coupled together such that the combined potential difference of the plurality of sensors can indicate a level of NO less than about 100 ppb in the breath sample.

13. The method of sensing NO as set forth in claim 12, further comprising determining a level of NO within the breath sample based on the combined potential difference generated by the plurality of sensors.

14. The method of sensing NO as set forth in claim 12, further comprising warming the sensing element.

15. The method of sensing NO as set forth in claim 12, wherein humidifying the breath sample comprises passing the breath sample through a liquid fluid to result in the humidified sample.

16. The method of sensing NO as set forth in claim 12, wherein passing the breath sample through the liquid fluid comprises bubbling the original sample through the liquid fluid.

17. The method of sensing NO as set forth in claim 12, wherein the plurality of sensors are electrically connected together in series.

18. The method of sensing NO as set forth in claim 17, wherein each of the plurality of sensors includes a sensing electrode and a reference electrode,
    wherein the sensing element further comprises:
        a first electrical lead electrically coupled to the sensing electrode of a first sensor of the plurality of sensors electrically connected together in series;
        a second electrical lead electrically coupled to the reference electrode of a last sensor of the plurality of sensors electrically connected together in series; and
    wherein the combined potential difference of the plurality of sensors is measurable between the first and second electrical leads.

19. An NO sensing system for measuring NO in a breath sample, the system comprising:
    an inlet for receiving the breath sample from a subject;
    means for humidifying the breath sample above a predetermined level resulting in a humidified breath sample; and
    a sensing element comprising a plurality of sensors electrically coupled together in series, each of the plurality of sensors configured to generate a potential difference in response to presence of NO in the humidified breath sample;
    wherein the plurality of sensors comprises an effective number of sensors coupled together in series such that a combined potential difference of the plurality of sensors can indicate a level of NO less than about 100 ppb in the breath sample.

20. The NO sensing system as set forth in claim 19, further including:
    a heater warming the sensor to be within a range of about 450° C. and about 650° C.

* * * * *